United States Patent
Joshi et al.

(10) Patent No.: US 9,895,318 B2
(45) Date of Patent: Feb. 20, 2018

(54) PHARMACEUTICAL OR NUTRACEUTICAL COMPOSITION WITH SUSTAINED RELEASE CHARACTERISTIC AND WITH RESISTANCE AGAINST THE INFLUENCE OF ETHANOL

(71) Applicants: Shraddha Sanjeev Joshi, Navi Mumbai (IN); Priyanka Parab, Thane (IN); Harsh Shah, Ahmedabad (IN); Preeti Patil, Mumbai (IN); Smitha Shetty, Mumbai (IN)

(72) Inventors: Shraddha Sanjeev Joshi, Navi Mumbai (IN); Priyanka Parab, Thane (IN); Harsh Shah, Ahmedabad (IN); Preeti Patil, Mumbai (IN); Smitha Shetty, Mumbai (IN)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 15/117,062

(22) PCT Filed: Feb. 9, 2015

(86) PCT No.: PCT/EP2015/052610
§ 371 (c)(1),
(2) Date: Aug. 5, 2016

(87) PCT Pub. No.: WO2015/121189
PCT Pub. Date: Aug. 20, 2015

(65) Prior Publication Data
US 2016/0354319 A1  Dec. 8, 2016

(30) Foreign Application Priority Data
Feb. 17, 2014 (IN) .............. 738/CHE/2014

(51) Int. Cl.
*A61K 9/50* (2006.01)
*A61K 9/16* (2006.01)
*A61K 31/138* (2006.01)
*A61K 31/522* (2006.01)

(52) U.S. Cl.
CPC .......... *A61K 9/5073* (2013.01); *A61K 9/1652* (2013.01); *A61K 9/1676* (2013.01); *A61K 9/5026* (2013.01); *A61K 9/5031* (2013.01); *A61K 9/5036* (2013.01); *A61K 9/5047* (2013.01); *A61K 31/138* (2013.01); *A61K 31/522* (2013.01); *A61K 9/5078* (2013.01)

(58) Field of Classification Search
None
See application file for complete search history.

(56) References Cited

U.S. PATENT DOCUMENTS

| | | | |
|---|---|---|---|
| 6,365,148 B1 * | 4/2002 | Kim ..................... | A61K 35/744 424/490 |
| 2011/0217383 A1 * | 9/2011 | Bar ...................... | A61K 9/5078 424/494 |
| 2012/0093926 A1 * | 4/2012 | Bodinge .............. | A61K 9/2846 424/463 |
| 2012/0321716 A1 | 12/2012 | Vachon et al. | |

FOREIGN PATENT DOCUMENTS

| | | |
|---|---|---|
| WO | 2012/022498 A1 | 2/2012 |
| WO | 2012/112952 A1 | 8/2012 |

OTHER PUBLICATIONS

International Search Report and Written Opinion of the International Searching Authority dated Apr. 14, 2015 in PCT/EP2015/052610 filed Feb. 9, 2015.

* cited by examiner

*Primary Examiner* — Isaac Shomer
(74) *Attorney, Agent, or Firm* — Grüneberg and Myers PLLC

(57) ABSTRACT

The invention refers to a pharmaceutical or nutraceutical composition, comprising a) a core, comprising a pharmaceutical or a nutraceutical active ingredient, b) an inner coating layer comprising one or more salts of alginic acid and c) an outer coating layer comprising one or more water-insoluble polymers or copolymers and one or more water-soluble polymers, selected from the group of water soluble celluloses, polyvinyl pyrrolidones or polyethylene glycols or any combinations thereof. wherein the ratio by weight of the amount of the one or more salts of alginic acid in the inner coating layer to the amount of the one or more water-insoluble polymers or copolymers in outer coating layer is from 0.6 to less than 2.5:1.

21 Claims, No Drawings

PHARMACEUTICAL OR NUTRACEUTICAL COMPOSITION WITH SUSTAINED RELEASE CHARACTERISTIC AND WITH RESISTANCE AGAINST THE INFLUENCE OF ETHANOL

TECHNICAL BACKGROUND

US 2007/0104789 A1 describes gastro-resistant and ethanol-resistant controlled-release formulations comprising hydromorphone. The gastro-resistant and ethanol-resistant can be used in a matrix as well as the coating of the formulations. Alginic acid is mentioned among the examples for suitable gastro-resistant and -ethanol resistant substances. Pellet cores or granules may be prepared by anhydrous granulation, may be coated with the gastro-resistant and ethanol-resistant substances and then may be filled in capsules or bags or compressed into tablets under addition of dried pharmaceutical or nutraceutically acceptable auxiliary substances.

WO 2012/022498 describes a gastric resistant pharmaceutical or nutraceutical composition, comprising a core, comprising a pharmaceutical or nutraceutical active ingredient and a gastric resistant coating layer onto the core, wherein the release of the pharmaceutical or nutraceutical active ingredient is not more than 15% under in-vitro conditions at pH 1.2 for 2 hours in a buffered medium according to USP with and without the addition of 40% (v/v) ethanol, wherein the gastric resistant coating layer comprises 10 to 100% by weight of one or more salts of alginic acid with a viscosity of 30 to 720 cP of a 1% aqueous solution. The one layer system as described solves the problem protection against the influence of ethanol. However except for coatings which include the ammonium alginate, coatings which employ other alginate salts, like sodium or potassium alginate, show no resistance against the influence of calcium ions at the same time.

OBJECT OF THE INVENTION

Pharmaceutical or nutraceutical compositions are designed to release the active ingredient in a manner of reproducible release curves. This shall result in desirable and reliable blood level profiles which shall provide an optimal therapeutic effect. If the blood level concentrations are too low, the active ingredient will not cause a sufficient therapeutic effect. If the blood level concentrations are too high, this may cause toxic effects. In both cases non optimal blood level concentrations of an active ingredient can be dangerous for the patient and shall therefore be avoided. A problem exists in that the ideal ratios assumed for the release of active ingredient during the design of a pharmaceutical or nutraceutical composition can be altered by the general living habits, thoughtlessness or by addictive behaviour of the patients with respect to the use of ethanol or ethanol-containing drinks. In these cases, the pharmaceutical or nutraceutical form which is actually designed for an exclusively aqueous medium is additionally exposed to an ethanol containing medium of greater or lesser strength. Since health authorities like for instance the US Food and Drug Administration (FDA) focus more and more on the ethanol problem, ethanol resistance may be an important registration requirement in the near future.

Since not all patients are aware of the risk of simultaneous taking of a controlled release pharmaceutical or nutraceutical form and ethanol-containing drinks or do not follow or are not able to follow appropriate warnings, advice or recommendations, there is a demand for controlled release pharmaceutical or nutraceutical compositions, especially for extended or sustained release pharmaceutical or nutraceutical compositions, such that their mode of action is affected as little as possible by the presence of ethanol.

Conventional extended or sustained release pharmaceutical or nutraceutical compositions if coated or uncoated are usually not resistant to alcohol at all. Therefore one problem of the present invention was to provide extended or sustained release pharmaceutical or nutraceutical compositions which are resistant against the influence of ethanol.

Especially there is a problem for compositions formulated for sustained release. These kinds of formulations are usually coated with water-insoluble polymers or copolymers onto a core comprising a pharmaceutical or nutraceutical active ingredient. The release of the pharmaceutical or nutraceutical active ingredient is sustained which means more or less constantly over the time (zero order release) and independent from the pH of the environment. The release of the pharmaceutical or nutraceutical active ingredient under in-vitro conditions after 2 hours at pH 1.2 in simulated gastric fluid according to USP (for instance USP 32) and subsequent change of the medium to buffered medium of pH 6.8 according to USP may for instance be in the range of 30 to 90, 40 to 80% in a total time, including the 2 hours of the pH 1.2 phase, of 4 to 12 or 4 to 8 hours.

However the presence of ethanol in concentrations of 5, 10, 20 or 40% (volume/volume) in the gastric fluid usually leads to an increase to the release rates already in the stomach. Thus an effective protection against the influence of ethanol should prevent such an undesired increase of pharmaceutical or nutraceutical active ingredient in the stomach but also in the intestine.

Thus the presence of ethanol in concentrations of 5, 10, 20 or 40% (volume/volume) under in-vitro conditions after 2 hours at pH 1.2 in simulated gastric fluid according to USP (for instance USP 32) shall not severely influence the intended sustained or extended release rates at pH 1.2.

Furthermore the presence of ethanol in concentrations of 5, 10, 20 or 40% (volume/volume) under in-vitro conditions after 2 hours at pH 1.2 in simulated gastric fluid according to USP (for instance USP 32) and subsequent change of the medium to buffered medium of pH 6.8 according to USP with or without ethanol shall not severely influence the intended sustained or extended release rates at pH 6.8.

Salts of alginates are generally able to be cross linked via calcium ions in aqueous media and can build up hydro gel like structures. Thus active ingredient release profile of a pharmaceutical or nutraceutical composition which comprises salts of alginates may be influenced in a negative way in the presence of calcium ions. One further object of the present invention is to provide a pharmaceutical or nutraceutical composition with a release profile which is not or only slightly influenced in situations where considerable amounts of calcium ions are present in the food and are ingested together with the pharmaceutical or nutraceutical composition. This can for instance happen when dairy products such like milk or yoghurt are consumed simultaneously. Surprisingly it has been found that the presence of calcium ion in USP enteric fluid and buffer pH 6.8 has almost no influence on the release rate of coatings in which the inventive pharmaceutical or nutraceutical composition is used.

It was therefore another object of the present invention to provide a pharmaceutical or nutraceutical composition for sustained or extended release with a release profile which is resistant against the influence of ethanol and also resistant against the influence of calcium ions.

Thus the presence of calcium ions in a concentration of 1.25 mM under in-vitro conditions after 2 hours at pH 1.2 in simulated gastric fluid according to USP (for instance USP 32) shall not severely influence the intended sustained release or extended rates at pH 1.2.

Furthermore the presence of calcium ions in a concentration of 1 mM under in-vitro conditions after 2 hours at pH 1.2 in simulated gastric fluid according to USP (for instance USP 32) and subsequent change of the medium to buffered medium of pH 6.8 according to USP with or without 1.25 mM calcium ions shall not severely influence the intended sustained or extended release rates at pH 6.8.

The objects are solved by a pharmaceutical or nutraceutical composition, comprising, comprising essentially or consisting of
- a) a core, comprising a pharmaceutical or a nutraceutical active ingredient,
- b) an inner coating layer comprising one or more salts of alginic acid and
- c) an outer coating layer comprising
  one or more water-insoluble polymers or copolymers and
  one or more water-soluble polymers, selected from the group of water soluble celluloses, polyvinyl pyrrolidones or polyethylene glycols or any combinations thereof, wherein the ratio by weight of the amount of the one or more salts of alginic acid in the inner coating layer to the amount of the one or more water-insoluble polymers or copolymers in outer coating layer is from 0.6 to less than 2.5:1.

DETAILED DESCRIPTION OF THE INVENTION

The invention relates to a pharmaceutical or nutraceutical composition, comprising
- a) a core, comprising a pharmaceutical or a nutraceutical active ingredient,
- b) an inner coating layer comprising one or more salts of alginic acid and
- c) an outer coating layer comprising
  one or more water-insoluble polymers or copolymers and
  one or more water-soluble polymers, selected from the group of water soluble celluloses, polyvinyl pyrrolidones or polyethylene glycols or any combinations thereof, wherein the ratio by weight of the amount of the one or more salts of alginic acid in the inner coating layer to the amount of the one or more water-insoluble polymers or copolymers in outer coating layer may be from (0.6 to less than 2.5):1, (0.6 to less than 2.2):1, (0.6 to less than 1.5):1, preferably (0.7 to less than 2.5):1, (0.6 to 2.2):1, (0.6 to 1.5):1, (0.7 up to less than 2.5):1.

Sustained or Extended Release Pharmaceutical or Nutraceutical Composition

The pharmaceutical or nutraceutical composition as disclosed herein is a sustained release or extended release pharmaceutical or nutraceutical composition.

The (sustained or extended) release of the pharmaceutical or nutraceutical active ingredient under in-vitro conditions after 2 hours at pH 1.2 in simulated gastric fluid according to USP (for instance USP 32) and subsequent change of the medium to buffered medium of pH 6.8 according to USP may be for instance in the range of 30 to 100, 40 to 80% in a total time, including the 2 hours of the pH 1.2 phase, of 4 to 12 or 4 to 8 hours.

Ethanol Resistant Pharmaceutical or Nutraceutical Composition

The pharmaceutical or nutraceutical composition as disclosed herein is an ethanol (EtOH) resistant pharmaceutical or nutraceutical composition.

Ethanol resistant shall mean that the active ingredient release of the pharmaceutical or nutraceutical composition in % under in-vitro conditions in a pH 1.2 medium (according to USP) for 2 hours and subsequent change to a buffered medium pH 6.8 (according to USP) without the addition of ethanol does not differ by more than plus/minus 20% (absolute percentage) in the same media but with the addition of 40% (v/v) ethanol in the pH 1.2 medium.

To give an example if the release rate of the pharmaceutical or nutraceutical active ingredient is in the medium without ethanol for instance 60% then the active ingredient release in the same medium with ethanol shall be in the range from 40 to 80% (+/−20% deviation).

Calcium Resistant Pharmaceutical or Nutraceutical Composition

The pharmaceutical or nutraceutical composition as disclosed is a calcium resistant pharmaceutical or nutraceutical composition.

Calcium resistant shall mean that the active ingredient release of the pharmaceutical or nutraceutical composition in % of the pharmaceutical or nutraceutical active ingredient under in-vitro conditions in a pH 1.2 medium for 2 hours and subsequent change to a buffered medium pH 6.0 without the addition of calcium ions does not differ by more than plus/minus 20 (absolute percentage) in the same media but with the addition of 1.25 mM calcium ions ($Ca^{++}$) in the pH 1.2 medium and optionally with the addition of 1.25 mM calcium ions ($Ca^{++}$) in the pH 1.2 medium and subsequent change to a buffered medium pH 6.0 with the addition of calcium ions.

To give an example if the release rate of the pharmaceutical or nutraceutical active ingredient is in the medium without calcium ions for instance 60% at a certain time, then the active ingredient release in the same medium with the addition of 1.25 mM calcium ions shall be at the same time in the range from 40 to 80% (+/−20% deviation).

Core

The core is comprising, comprising essentially or consisting of a pharmaceutical or a nutraceutical active ingredient.

The core may comprise or may contain a neutral carrier pellet, for instance a sugar sphere or non-pareilles, on top of which the active ingredient may be bound in a binder, such as lactose, celluloses, like micro crystalline cellulose (MCC), or polyvinylpyrrolidon (PVP). In this case the active ingredient may be bound or placed localized at the surface of the core (as a part of the core). The binding of the active ingredient at the surface of the core in such a binding layer has usually no effect or influence in the sense of a release control function.

The core may alternatively comprise a pellet in the form of a polymeric matrix in which the active ingredient is bound. The core may comprise an uncoated pellet or granule consisting of a crystallized active ingredient. The core may be as well an active ingredient containing tablet, mini tablet or capsule. In these cases the active ingredient may be placed more or less randomly distributed throughout the core as a whole.

Coating Layers

The pharmaceutical or nutraceutical composition is comprising, comprising essentially or consisting of the core, the inner coating layer onto the core and the outer coating layer onto the inner coating layer as claimed.

The coating layers have the function of controlling the release of the active ingredient, which is placed in the core or at the surface of the core. The coating layers have also the function of providing resistance of the release rates against the presence ethanol or against the presence of calcium ions.

Preferably the pharmaceutical or nutraceutical composition is comprising, comprising essentially or consisting of the core, the inner coating layer and the outer coating layer as claimed and there are no further coating layers present, which would additionally control the release of the active ingredient.

The Inner Coating Layer

The inner coating layer is located onto the core. A sub coat may be located between the core and the inner coating layer. A sub coat may have the function to separate substances of the core from substances of the controlling layer which may be incompatible with each other. The sub coat has essentially no influence on the active ingredient release characteristics. Preferably there is no sub coat between the core and the inner coating layer. In this case the inner coating layer is in direct contact with core.

The inner coating layer may comprise at least 10, at least 20 at least 30, at least 40, at least 50, at least 60, at least 70, at least 80, at least 90% by weight of one or more salts of alginic acid.

The salts of alginic acid may be selected from sodium alginate, potassium alginate, magnesium alginate, lithium alginate or ammonium alginate or mixtures thereof.

The salts of alginic acid used for the inner coating layer may preferably have a viscosity of 30 to 720 cP of a 1% aqueous solution (weight/weight).

The amount of the inner coating layer calculated on the weight of the core is preferably at least equal or higher than the amount of the outer coating layer The total amount of the inner coating layer may be in the range of 10 to 100, 15 to 80, 20 to 70 or 30 to 60% by weight in relation to the weight of the core.

The absolute amount of polymer the inner coating layer may be in the case of pellets or granules with a size in the range of 50 to 1000 μm (average diameter) in the range of 2 to 50, preferably 5 to 40 mg/cm$^2$.

The absolute amount of polymer in the inner coating layer may be in the case of tablets with a size in the range of more than 1 and up to 25 mm (Average diameter or length) in the range of 0.5 to 10, preferably 1 to 6 mg/cm$^2$.

When the inner and the outer coating layer are calculated together as 100% the amount of the inner coating layer may be at least 50% by weight or more, at least 60% by weight or more, at least 70% by weight or more, at least 80% by weight or more, at least 90% by weight or more in relation to both coating layers.

The inner coating layer may comprise up to 70, up to 60, up to 50, up to 40, up to 30, up to 20, up to 10% or any (0%) by weight of pharmaceutical or nutraceutically acceptable excipients. The pharmaceutical or nutraceutically acceptable excipients in the inner coating layer are different from the salts of alginic acid. Preferably the inner coating layer comprises less than 10% by weight, less than 5% by weight, less than 1% by weight or any (0%) water-insoluble polymers or copolymers.

A typical inner coating may for example comprise or contain 40-60% by weight of one or more salts of alginic acid and 40 to 60% by weight of a glidant, for instance talc.

The Outer Coating Layer

The outer coating layer is located onto the inner coating layer.

The outer coating may comprise 20-90% by weight of the one or more water-insoluble polymers or copolymers, 1-40% by weight of the one or more water-soluble polymers, selected from the group of water soluble celluloses, polyvinyl pyrrolidones or polyethylene glycols or any combinations thereof and optionally up to 20% of the one or more emulsifiers and optionally up to 60% by weight of pharmaceutical or nutraceutically acceptable excipients.

All components add up to 100%.

A sub coat may be located between the inner coating layer and outer coating layer. The sub coat has essentially no influence on the active ingredient release characteristics. Preferably there is no sub coat between the core and the inner coating layer. In this case the outer coating layer is in direct contact with the inner coating layer.

A top coat may be located on top of the outer coating layer. The top coat may be preferably water-soluble, essentially water-soluble or dispersible. A top coat may have the function of colouring the pharmaceutical or nutraceutical form or protecting from environmental influences for instance from moisture during storage. The top coat may consist out of a binder, for instance a water soluble polymer like a polysaccharide or HPMC, or a sugar compound like saccharose. The top coat may further contain pharmaceutical or nutraceutical excipients like pigments or glidants in high amounts. The topcoat has essentially no influence on the release characteristics. Preferably there is no top coat onto the outer coating layer.

The pharmaceutical or nutraceutical composition may be characterised in that there are except for the inner coating layer and the outer coating layer no further controlling layers present which control the release the pharmaceutical or a nutraceutical active ingredient.

The outer coating layer may comprise 20-99, 25-85 or 30-60% by weight of one or more water-insoluble polymers or copolymers.

The outer coating layer may comprise 1-40, 10-30 or 15 to 25% by weight of the one or more water-soluble polymers, selected from the group of water soluble celluloses, polyvinyl pyrrolidones or polyethylene glycols or any combinations thereof.

The outer coating layer may comprise up to up to 60, up to 50, 0-60, 1-50, 2-40, 5-35% by weight or any (0% by weight) of pharmaceutical or nutraceutically acceptable excipients. The pharmaceutical or nutraceutically acceptable excipients in the outer coating layer are different from the water-insoluble polymers or copolymers and the water-soluble celluloses. Preferably the outer coating layer comprises less than 10% by weight, less than 5% by weight, less than 1% by weight or any (0%) salts of alginic acid.

The total amount of the outer coating layer may be in the range of 10 to 100, 15 to 80, 20 to 70 or 30 to 60% by weight in relation to the weight of the core.

The absolute amount of polymer the outer coating layer may be in the case of pellets or granules with a size in the range of 50 to 1000 μm (average diameter) in the range of 1 to 25, preferably 2.5 to 20 mg/cm$^2$.

The absolute amount of polymer in the outer coating layer may be in the case of tablets with a size in the range of more than 1 and up to 25 mm (average diameter or length) in the range of 0.25 to 5, preferably 0.5 to 3 mg/cm$^2$.

Water-Insoluble Polymers or Copolymers

Water-insoluble polymers in the sense of the invention are polymers or copolymers which do not dissolve in water or are only swellable in water over of the whole range of pH 1-14. Water-insoluble polymers may be at the same time polymers containing not more than 12% of polymerized monomers with ionic side groups, like for instance the types of EUDRAGIT® NE/NM or EUDRAGIT® RL/RS polymers.

The water-insoluble polymers may preferably belong to the group of (meth)acrylate copolymers.

Other kinds of water-insoluble polymers in the sense of the invention may be vinyl copolymers like polyvinylacetate, including derivates of polyvinylacetate. The polyvinylacetate may be present in the form of a dispersion. One example is the type Kollicoat® SR 30 D (BASF), polyvinylacetate dispersion, stabilized with povidone and Na-laurylsulfate. The amount of the water-insoluble polymers in the outer coating layer may be in the range of 20-99, 25-85 or 30-60% by weight.

EUDRAGIT® NE 30D/EUDRAGIT® NM 30D-Type Polymers

The outer coating layer may comprise a water-insoluble copolymer which is a copolymer composed of free-radical polymerized units of more than 95% by weight, in particular to an extent of at least 98% by weight, preferably to an extent of at least 99% by weight, in particular to an extent of at least 99.5% by weight, more preferably to an extent of 100% by weight, of (meth)acrylate monomers with neutral radicals, especially $C_1$- to $C_4$-alkyl radicals. These kinds of polymers do not dissolve in water or are only swellable in water over of the whole range of pH 1-14.

Suitable (meth)acrylate monomers with neutral radicals are, for example, methyl methacrylate, ethyl methacrylate, butyl methacrylate, methyl acrylate, ethyl acrylate, butyl acrylate. Preference is given to methyl methacrylate, ethyl acrylate and methyl acrylate.

Methacrylate monomers with anionic radicals, for example acrylic acid and/or methacrylic acid, may be present in small amounts of less than 5% by weight, preferably by not more than 2% by weight, more preferably by not more than 1 or by 0.05 to 1 or by 0 to 0.5% by weight.

Suitable examples are neutral or virtually neutral (meth) acrylate copolymers composed of 20 to 40% by weight of ethyl acrylate, 60 to 80% by weight of methyl methacrylate and 0 to less than 5% by weight, preferably 0 to 2 or 0.05 to 1% or by 0 to 0.5% by weight of methacrylic acid or any methacrylic acid (EUDRAGIT® NE 30D or EUDRAGIT® NM 30D type).

EUDRAGIT® NE 30D and Eudragit® NM 30D are dispersions containing 30% by weight of copolymers composed of free-radically polymerized units of 30% by weight of ethyl acrylate and 70% by weight of methyl methacrylate.

Preference is given to neutral or essentially neutral methyl acrylate copolymers which, according to WO 01/68767, have been prepared as dispersions using 1-10% by weight of a nonionic emulsifier having an HLB value of 15.2 to 17.3. The latter offer the advantage that there is no phase separation with formation of crystal structures by the emulsifier (Eudragit® NM 30D type).

According to EP 1 571 164 A2, corresponding, virtually neutral (meth)acrylate copolymers with small proportions of 0.05 to 1% by weight of monoolefinically unsaturated C3-C8-carboxylic acids can, however, also be prepared by emulsion polymerization in the presence of comparatively small amounts of anionic emulsifiers, for example 0.001 to 1% by weight.

EUDRAGIT® RL/RS-Type Polymers

The outer coating layer may comprise a water-insoluble copolymer which is a copolymer composed of free-radical polymerized units of 85 to 98% by weight of free-radical polymerized $C_1$ to $C_4$ alkyl esters of acrylic or methacrylic acid and 15 to 2% by weight of (meth)acrylate monomers with a quaternary ammonium group in the alkyl radical. These kinds of polymers do not dissolve in water or are only swellable in water over of the whole range of pH 1-14.

Water in-Soluble Celluloses

Suitable water-insoluble polymers or copolymers may belong to the group of cellulosic polymers, preferably to the group of water-insoluble celluloses. A suitable water-insoluble cellulosic polymer is ethyl cellulose (EC).

Vinyl Copolymers

Other kinds of water-insoluble polymers in the sense of the invention may be vinyl copolymers like polyvinylacetate, including derivates of polyvinylacetate. The polyvinylacetate may be present in the form of a dispersion. One example is the type Kollicoat® SR 30 D (BASF), polyvinylacetate dispersion, stabilized with Povidone® and Na-laurylsulfate.

Water-Soluble Polymers

The outer coating layer is comprising one or more water-insoluble polymers or copolymers and one or more water-soluble polymers, selected from the group of water soluble celluloses, polyvinyl pyrrolidones or polyethylene gylcols or any combinations thereof.

A water-soluble polymer in the sense of the invention is a polymer which is soluble in water, preferably in demineralized water, without addition of acids or bases. A water-soluble polymer may be defined in that it needs 1 to 10, 10 to 30, 30 to 100 g of water to dissolve 1 g of the polymer at 15 to 25° C., for instance at 20° C. For instance polymers with pH-dependent solubility in water are not water-soluble in the sense of the invention. The one or more water-soluble polymers are selected from the group of water soluble celluloses, polyvinyl pyrrolidones or polyethylene gylcols or any combinations thereof.

The amount of the water-soluble polymers in the outer coating layer may be in the range of 1-40, 2-25, 2-10 or 3-8% by weight.

Water-Soluble Celluloses

The outer coating layer may comprise one or more water-soluble celluloses.

The one or more water-soluble celluloses may be preferably selected from the group of water-soluble methyl-, ethyl or propyl-ethers of cellulose or any combinations thereof.

The one or more water-soluble celluloses may be are selected from the group of methyl celluloses, hydroxy-methyl-celluloses, hydroxy-ethyl-celluloses, hydroxy-ethyl-methyl-celluloses, hydroxy-propyl-celluloses (HPC), hydroxy-methyl-propyl-celluloses (HPMC), ethyl-hydroxy-ethyl-celluoses, carboxy-methyl-celluloses, carboxy-methyl-ethyl celluloses, sodium-carboxy-methyl-celluloses or any combinations thereof.

Polyvinylpyrrolidones

The outer coating layer may comprise one or more water-soluble, preferably non-cross-linked polyvinylpyrrolidones. The preferred molecular weight (Mw) of water-soluble polyvinylpyrrolidones may be in the range of 2.500-2.500.000, 5.000-250.000, 10.000-50.000 g/mol. Analytical methods to determine the molecular weight ($M_w$=average weight molecular weight) are well known to a skilled person. In general molecular weight $M_w$ can be determined by gel permeation chromatography or by a light-scattering method (see, for example, H. F. Mark et al., Encyclopedia of Polymer Science and Engineering, 2nd Edition, Vol. 10, pages 1 ff., J. Wiley, 1989).

Polyethylene Glycols

The outer coating layer may comprise one or more water-soluble polyethylene glycols. The term polyethylene glycols in the sense of the invention refers to polymers often named as polyethylen glycols (PEG), polyethylenoxide (PEO) or polyoxyethylen (POE) which refer to oligomers or polymers of ethylene oxide. The three names are chemically synonymous, but historically PEG has tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. PEGs are prepared by polymerization of ethylene oxide and are commercially available over a wide range of molecular weights from 300 g/mol to 10,000,000 g/mol (Source of information: Wikipedia). Preferred molecular weights (Mw) of water-soluble polyethylene glycols may be in the range of 300-100.000, 300-25.000 or 300-15.000 g/mol.

Properties of the Pharmaceutical or Nutraceutical Composition

The pharmaceutical or nutraceutical composition may be characterized in that wherein the release of the pharmaceutical or nutraceutical active ingredient in % under in-vitro conditions in a pH 1.2 medium (according to USP, for instance USP 32) for 2 hours and subsequent change to a buffered medium pH 6.8 (according to USP, for instance USP 32) without the addition of ethanol does not differ by more than plus/minus 20% (absolute percentage) in the same media but with the addition of 5, 10, 20 or 40% (v/v) ethanol in the pH 1.2 medium. If for example the release of the pharmaceutical or nutraceutical active ingredient in the media (pH 1.2 or pH 6.8) without ethanol is 40%, then the release in media with 5, 10, 20 or 40% (v/v) ethanol shall be in the range of 20 to 60% (40+/−20%) to be acceptable.

The release of the pharmaceutical or nutraceutical active ingredient in % under in-vitro conditions in pH 1.2 medium for 2 hours according to USP and subsequent buffer pH 6.8 medium according to USP without the addition of ethanol does preferably not differ by more than plus/minus 20% (absolute percentage) in the same media with the addition of 40% (v/v) ethanol.

The pharmaceutical or nutraceutical composition may be characterized in the release in % of the pharmaceutical or nutraceutical active ingredient under in-vitro conditions in a pH 1.2 medium (according to USP, for instance USP 32) for 2 hours and subsequent change to a buffered medium pH 6.0 (according to USP, for instance USP 32) without the addition of calcium ions does not differ by more than plus/minus 20 (absolute percentage) in the same media but with the addition of 1.25 mM calcium ions ($Ca^{++}$) in the pH 1.2 medium.

The release of the pharmaceutical or nutraceutical active ingredient under in-vitro conditions in pH 1.2 medium for 2 hours according to USP and subsequent buffer pH 6.0 medium without the addition of calcium ions does preferably not differ by more than plus/minus 20 (absolute percentage) in the same media with the addition of 1.25 mM calcium ions.

The pharmaceutical or nutraceutical composition may be characterized in that release of the pharmaceutical or nutraceutical active under in-vitro conditions after 2 hours at pH 1.2 in simulated gastric fluid and subsequent change of the medium to buffered medium of pH 6.8 according to USP is 30 to 90 or 40 to 80% in a total time from 4 to 16 or 4 to 12 or 4 to 8 hours. The term "total time" in this case shall include the 2 hours pH 1.2 phase. Thus a "total time" of 4 hours shall mean 2 hours at pH 1.2 plus 2 hours at pH 6.8.

Salts of Alginic Acid

The salts of alginic acid may be selected from sodium alginate, potassium alginate, magnesium alginate, lithium alginate or ammonium alginate or any kind of mixtures thereof.

Viscosity

The salts of alginic acid may have a viscosity of 30 to 720, preferably 40 to 450, preferably 40 to 400 or preferably 50 to 300 centipoise (cp) of a 1% aqueous solution (weight/weight).

The methodology of determination of the viscosity of a polymer solution, for instance a solution of a salt of alginic acid, is well known to the skilled person. The viscosity is preferably determined according to European Pharmacopeia $7^{th}$ edition, general chapter 2, methods of analysis, 2.2.8 and 2.2.10, page 27ff. The test is performed using a spindle viscometer.

The viscosity of a 1% alginate solution may be determined by adding 3 g product to 250 ml of distilled water in a beaker while stirring at 800 rpm using overhead stirrer. Then additional 47 ml water was added with rinsing the walls of the beaker. After stirring for 2 hours and getting a complete solution, the viscosity is measured using a LV model of the Brookfield viscometer at 25° C. (77° F.) at 60 rpm with no. 2 spindle for samples with a viscosity of more than 100 cP and at 60 rpm with no. 1 spindle for samples with viscosity less than 100 cP. Since the weight of water is almost exactly 1 g/ml even at 25° C. "weight/weight" is regarded as equal or identical to "weight/volume" in the sense of the invention. Theoretically possible marginal differences are regarded as insignificant.

Emulsifiers

The outer coating may further comprise an emulsifier (in the sense of one or more emulsifiers). The emusifier is preferably a non-ionic emulsifier. Most preferably the emulsifier is a polyoxyethylene derivative of a sorbitan ester or a sorbitan ether. The amount of the emulsifier in the outer coating layer may be in the range of up to 20, 0-20, 1-20, 2-15, 2-12 or 2-8% by weight calculated on the weight of the water-insoluble polymer. The amount of the emulsifier in the outer coating layer may be in the range of up to 12, 0-12, 1-10 or 2-8% by weight calculated on the weight of the outer coating. There may be any emulsifier (0%) present in the outer coating layer as well.

Addition of Further Polymers to the Inner or to the Outer Coating Layer

The inner coating layer or the outer coating layer of the pharmaceutical or nutraceutical composition may further comprise additionally, one or more polymers or copolymers with neutral or ionic side groups different from the one or more salts of alginic acid, respectively different from the one or more water-insoluble polymers or copolymers and different from the water-soluble polymers, which are selected from the group of water soluble celluloses, polyvinyl pyrrolidones or polyethylene glycols or any combinations thereof.

For instance one or more of such additional or further polymers or copolymers with neutral or ionic side groups respectively may be comprised or contained in the inner coating layer or the outer coating layer respectively as long as the properties of the pharmaceutical or nutraceutical composition as disclosed herein are not influenced negatively.

Further polymers or copolymers with neutral or ionic side groups which may be comprised or contained additionally the inner or to the outer coating layer may belong to the groups of anionic vinyl polymers or anionic (meth)acrylate copolymers.

Usually the inner coating layer or the outer coating layer may comprise or contain less than 10, less than 5, less than 2, less than 1% by weight or any (0%) of these further polymers or copolymers with neutral or ionic side groups respectively calculated either on the content one or more salts of alginic acid in the inner coating layer or respectively on the content of the one or more water-insoluble polymers or copolymers in the outer coating layer. As a rule it is preferred that the inner coating layer and/or the outer coating layer of the pharmaceutical or nutraceutical composition do not comprise or contain any of such additional further polymers or copolymers.

Anionic Polyvinyl Polymers as Further Polymers

Suitable polyvinyl polymers or copolymers may comprise structural units that are derived from unsaturated carboxylic acids other than acrylic acid or methacrylic acid as exemplified by polyvinylacetate-phthalate, a copolymer of vinylacetate and crotonic acid (preferably ratio 9:1) or polyvinylacetate-succinate Anionic (Meth)Acrylate Copolymers as Further Polymers Suitable anionic (meth)acrylate copolymers may comprise 25 to 95, preferably 40 to 95, in particular 60 to 40, % by weight free-radical polymerized $C_1$- to $C_{18}$-alkyl esters, preferably $C_1$- to $C_8$- or $C_1$- to $C_4$-alkyl esters alkyl esters of acrylic or of methacrylic acid and 75 to 5, preferably 60 to 5, in particular 40 to 60, % by weight (meth)acrylate monomers having an anionic group.

The monomer proportions mentioned normally add up to 100% by weight. However it is also possible in addition, without this leading to an impairment or alteration of the essential properties, for small amounts in the region of 0 to 10, for example 1 to 5, % by weight of further monomers capable of vinylic copolymerization, such as, for example, hydroxyethyl methacrylate or hydroxy-ethyl acrylate, to be present. It is preferred that no further monomers capable of vinylic copolymerization are present.

$C_1$- to $C_4$-alkyl esters of acrylic or methacrylic acid are in particular methyl methacrylate, ethyl methacrylate, butyl methacrylate, methyl acrylate, ethyl acrylate and butyl acrylate.

Pharmaceutical or Nutraceutical Active Ingredient
Nutraceuticals

The invention is preferably useful for nutraceutical dosage forms.

Nutraceuticals can be defined as extracts of foods claimed to have medical effects on human health. The nutraceutical is usual contained in a medical format such as capsule, tablet or powder in a prescribed dose. Examples for nutraceuticals are resveratrol from grape products as an antioxidant, soluble dietary fiber products, such as psyllium seed husk for reducing hypercholesterolemia, broccoli (sulphane) as a cancer preservative, and soy or clover (isoflavonoids) to improve arterial health. Other nutraceuticals examples are flvonoids, antioxidants, alpha-linoleic acid from flax seed, beta-carotene from marigold petals or antocyanins from berries. Sometimes the expression neutraceuticals is used as synonym for nutraceuticals.

The Sustained or Extended Release Pharmaceutical or Nutraceutical Composition is Comprising a core, comprising a pharmaceutical or nutraceutical active ingredient. The pharmaceutical or nutraceutical active ingredient may be a pharmaceutical or nutraceutical active ingredient which may be inactivated under the influence of gastric fluids at pH 1.2 or a pharmaceutical or nutraceutical active ingredient which may irritate the stomach mucosa when set free in the stomach.

Pharmaceutical Active Ingredients

The invention is preferably useful for sustained release formulated pharmaceutical dosage forms.

Therapeutical and chemical classes of drugs used in sustained release formulated coated pharmaceutical dosage forms are for instance analgetics, antibiotics or anti-infectives, antibodies, antiepileptics, antigens from plants, anti-rheumatics, betablocker, benzimidazole derivatives, beta-blocker, cardiovascular drugs, chemotherapeuitcs, CNS drugs, digitalis glycosides, gastrointestinal drugs, e.g. proton pum inhibitors, enzymes, hormons, liquid or solid natural extracts, oligonucleotides, peptidhormon proteins, therapeutical bacteria, peptides, proteins, proton pump inhibitors, (metal) salt f.e. aspartates, chlorides, orthates, urology drugs, vaccines Further examples of drugs for sustained controlled release may be: acamprosat, aescin, amylase, acetylsalicylic acid, adrenalin, 5-amino salicylic acid, aureomycin, bacitracin, balsalazine, beta carotene, bicalutamid bisacodyl, bromelain, bromelain, budesonide, calcitonin, carbamacipine, carboplatin, cephalosporins, cetrorelix, clarithromycin, chloromycetin, cimetidine, cisapride, cladribine, clorazepate, cromalyn, 1-deaminocysteine-8-D-arginine-vasopressin, deramciclane, detirelix, dexlansoprazole, diclofenac, didanosine, digitoxin and other digitalis glycosides, dihydrostreptomycin, dimethicone, divalproex, drospirenone, duloxetine, enzymes, erythromycin, esomeprazole, estrogens, etoposide, famotidine, fluorides, garlic oil, glucagon, granulocyte colony stimulating factor (G-CSF), heparin, hydrocortisone, human growth hormon (hGH), ibuprofen, ilaprazole, insulin, Interferon, Interleukin, Intron A, ketoprofen, lansoprazole, leuprolidacetat lipase, lipoic acid, lithium, kinin, memantine, mesalazine, methenamine, milameline, minerals, minoprazole, naproxen, natamycin, nitrofurantion, novobiocin, olsalazine, omeprazole, orothates, pancreatin, pantoprazole, parathyroidhormone, paroxetine, penicillin, perprazol, pindolol, polymyxin, potassium, pravastatin, prednisone, preglumetacin progabide, pro-somatostatin, protease, quinapril, rabeprazole, ranitidine, ranolazine, reboxetine, rutosid, somatostatin streptomycin, subtilin, sulfasalazine, sulphanilamide, tamsulosin, tenatoprazole, thrypsine, valproic acid, vasopressin, vitamins, zinc, including their salts, derivatives, polymorphs, isomorphs, or any kinds of mixtures or combinations thereof.

Pharmaceutical or Nutraceutical Composition

The pharmaceutical or nutraceutical composition as disclosed herein may be a coated tablet, a coated minitablet, a coated pellet, a coated granule, a sachet, a capsule, filled with coated pellets or with powder or with granules, or a coated capsule, filled with coated pellets or with powder or with granules.

The term coated tablet includes pellet-containing tablets or compressed tablets and is well known to a skilled person. Such a tablet may have a size of around 5 to 25 mm for instance. Usually, defined pluralities of small active ingredient containing pellets are compressed therein together with binding excipients to give the well-known tablet form. After oral ingestion and contact with the body fluid the tablet form is disrupted and the pellets are set free. The compressed tablet combines the advantage of the single dose form for ingestion with the advantages of a multiple forms, for instance the dosage accuracy.

The term coated minitablet is well known to the skilled person. A minitablet is smaller than the traditional tablet and may have a size of around 1 to 4 mm. The minitablet is, like a pellet, a single dosage form to be used in multiple dosages. In comparison to pellets, which may be in the same size, minitablets usually have the advantage of having more regular surfaces which can be coated more accurately and more uniformly. Minitablets may be provided enclosed in capsules, such as gelatine capsules. Such capsules disrupt after oral ingestion and contact with the gastric or intestinal fluids and the minitablets are set free. Another application of minitablets is the individual fine adjustment of the active ingredient dosage. In this case the patient may ingest a defined number of minitablets directly which matches to the severe of the decease to cure but also to his individual body weight. A minitablet is different from pellet-containing compressed tablet as discussed above.

The term sachet is well known to the skilled person. It refers to small sealed package which contains the active ingredient often in pellet containing liquid form or also in dry pellet or powder form. The sachet itself is only the package form is not intended to be ingested. The content of the sachet may be dissolved in water or as an advantageous feature may be soaked or ingested directly without further liquid. The latter is advantageous feature for the patient when the dosage form shall be ingested in a situation where no water is available. The sachet is an alternative dosage form to tablets, minitablets or capsules.

Coated pellets may be filled in a capsule, for instance gelatine or HPMC capsule. A capsule containing pellets may also be coated with the enteric coating layer according to the invention. The extended or sustains release pharmaceutical or nutraceutical coating composition is preferably present in the form of an aqueous coating solution, suspension or dispersion. The dry weight content of the solution, suspension or dispersion may be in the range of 10 to 50, preferably 15 to 35%.

Pharmaceutical or Nutraceutically Acceptable Excipients

The Pharmaceutical or nutraceutical composition may comprise pharmaceutical or nutraceutically acceptable excipients selected from the group of antioxidants, brighteners, binding agents, flavouring agents, flow aids, fragrances, glidants, penetration-promoting agents, pigments, plasticizers (for instance dibutyl sebacate), polymers which are different from the polymers as already listed in Claim 1 under b) and c), pore-forming agents or stabilizers or combinations thereof. Excipient polymers may be for instance disintegrants like crosslinked polyvinyl pyrrolidone, pigments, plasticizers, pore-forming agents or stabilizers or combinations thereof. Disintegrants like crosslinked polyvinyl pyrrolidone may be excluded from the pharmaceutical or nutraceutical composition as well.

The pharmaceutical or nutraceutically acceptable excipients may be comprised in the core and/or in the inner coating layer and/or in the outer coating layer.

The inner coating layer comprises may comprise up to 70, up to 60, up to 50, up to 40%, up to 30, up to 20, up to 10, 0 to 70, 10 to 70, 20 to 60, 30 to 50, 0 to 10 by weight or any (0%) of pharmaceutical or nutraceutically acceptable excipients.

The outer coating layer comprises may comprise up to up to 60, up to 50, 0 to 60, 0 to 50, 0 to 10, 5 to 20, up to 20, up to 15, up to 10, up to 5 or any (0%) % by weight of pharmaceutical or nutraceutically acceptable excipients.

Process for Producing a Pharmaceutical or Nutraceutical Form

A suitable process for producing the pharmaceutical or nutraceutical composition as disclosed in here may be by forming the core comprising the active ingredient by direct compression, compression of dry, wet or sintered granules, by extrusion and subsequent rounding off, by wet or dry granulation, by direct pelleting or by binding powders onto active ingredient-free beads or neutral cores or active ingredient-containing particles and by applying the inner coating layer and the outer coating layer in the form of aqueous dispersions or organic solutions in spray processes or by fluidized bed spray granulation.

Top Coat and Sub Coats

The pharmaceutical or nutraceutical composition as disclosed herein may be further coated with a sub coat or a top coat or both.

A sub coat may be located between the core and the inner coating layer. A sub coat may have the function to separate substances of the core from substances of the controlling layer which may be incompatible with each other. The sub coat has essentially no influence on the active ingredient release characteristics. A subcoat is preferably essentially water-soluble, for instance it may consist of substances like hydroxypropylmethyl-cellulose (HPMC) as a film former. The average thickness of the subcoat layer is very thin, for example not more than 15 µm, preferably not more than 10 µm.

A top coat may be located on top of the outer coating layer. A top coat is also preferably essentially water soluble. A top coat may have the function of colouring the pharmaceutical or nutraceutical form or protecting from environmental influences for instance from moisture during storage. The top coat may consist out of a binder, for instance a water soluble polymer like a polysaccharide or HPMC, or a sugar compound like saccharose. The top coat may further contain pharmaceutical or nutraceutical excipients like pigments or glidants in high amounts. The topcoat has essentially no influence on the release characteristics.

The expressions sub coat and top coat are well known to the person skilled in the art.

Pellet/Granule/Tablet/Mintablet/Sachet/Capsule

Pharmaceutical or nutraceutical composition may be a coated tablet, a coated minitablet, a coated pellet, a coated granule, a sachet, a capsule, filled with coated pellets or with powder or with granules, or a coated capsule.

Pellets or granules may be used as cores or in compressed tablets. As a rough estimation pellets may have a size in the range of 50 to 1000 µm (average diameter), while coated tablets may have a size in the range of above 1000 µm up to 25 mm (diameter or length). As a rule one can say the smaller the size of the pellet cores are, the higher the pellet coating weight gain needed. This is due to the comparably higher surface area of pellets compared to tablets.

The term pellet-containing tablet or compressed tablet is well known to a skilled person. Such a tablet may have a size of around 5 to 25 mm for instance. Usually, defined pluralities of small active ingredient containing pellets are compressed therein together with binding excipients to give the well-known tablet form. After oral ingestion and contact with the body fluid the tablet form is disrupted and the pellets are set free. The compressed tablet combines the advantage of the single dose form for ingestion with the advantages of a multiple forms, for instance the dosage accuracy. In tablets coatings comparably low amounts of excipients, preferably talcum but also other excipients, may be used in contrast to pellets.

The term minitablet is well known to the skilled person. A minitablet is smaller than the traditional tablet and may have a size of around 1 to 4 mm. The minitablet is, like a pellet, a single dosage form to be used in multiple dosages. In comparison to pellets, which may be in the same size, minitablets usually have the advantage of having more regular surfaces which can be coated more accurately and more uniformly. Minitablets may be provided enclosed in capsules, such as gelatine capsules. Such capsules disrupt after oral ingestion and contact with the gastric or intestinal fluids and the minitablets are set free. Another application of minitablets is the individual fine adjustment of the active ingredient dosage. In this case the patient may ingest a defined number of minitablets directly which matches to the severe of the decease to cure but also to his individual body weight. A minitablet is different from pellet-containing compressed tablet as discussed above.

The term sachet is well known to the skilled person. It refers to small sealed package which contains the active ingredient often in pellet containing liquid form or also in dry pellet or powder form. The sachet itself is only the package form is not intended to be ingested. The content of the sachet may be dissolved in water or as an advantageous feature may be soaked or ingested directly without further liquid. The latter is advantageous feature for the patient when the dosage form shall be ingested in a situation where no water is available. The sachet is an alternative dosage form to tablets, minitablets or capsules.

The term capsule is well known to the skilled person. A capsule is like the sachet a container for pellets containing liquids or also dry pellets or powders. However in contrast to the sachet the capsule consists of pharmaceutically acceptable excipients such as gelatine or hydroxy-propyl-methyl-cellulose (HPMC) and is intended to be ingested like a tablet. The capsules disrupts after oral ingestion and contact with the gastric or intestinal fluids and the contained multiple units are set free. Capsules for pharmaceutical purposes are commercially available in different standardized sizes.

Use

The pharmaceutical or nutraceutical composition as described herein may be used as a sustained release or extended release pharmaceutical or nutraceutical composition with resistance against the influence of ethanol and optionally with resistance against the influence of calcium ions.

Summary of Items of the Invention

The invention is concerned with but not limited to following items:

1. Pharmaceutical or nutraceutical composition, comprising
   a) a core, comprising a pharmaceutical or a nutraceutical active ingredient,
   b) an inner coating layer comprising one or more salts of alginic acid and
   c) an outer coating layer comprising
      one or more water-insoluble polymers or copolymers and
      one or more water-soluble polymers, selected from the group of water soluble celluloses, polyvinyl pyrrolidones or polyethylene glycols or any combinations thereof,
   wherein the ratio by weight of the amount of the one or more salts of alginic acid in the inner coating layer to the amount of the one or more water-insoluble polymers or copolymers in outer coating layer is from 0.6 to less than 2.5:1.

2. Pharmaceutical or nutraceutical composition, according to item 1, wherein the total amount of the inner coating layer may be in the range of 10 to 100% by weight in relation to the weight of the core.
3. Pharmaceutical or nutraceutical composition, according to item 1 or 2, wherein there are, except for the inner coating layer and the outer coating layer, no further controlling layers present which control the release the pharmaceutical or a nutraceutical active ingredient.
4. Pharmaceutical or nutraceutical composition, according to any of items 1 to 3, wherein the one or more salts of alginic acid have a viscosity of 30 to 720 cP of a 1% aqueous solution (weight/weight).
5. Pharmaceutical or nutraceutical composition, according to one or more of items 1 to 4, wherein the inner coating layer comprises up to 70% by weight of pharmaceutical or nutraceutically acceptable excipients.
6. Pharmaceutical or nutraceutical composition, according to one or more of items 1 to 5, wherein the release of the pharmaceutical or nutraceutical active ingredient in % under in-vitro conditions in a pH 1.2 medium for 2 hours and subsequent change to a buffered medium pH 6.8 without the addition of ethanol does not differ by more than plus/minus 20% (absolute percentage) in the same media but with the addition of 40% (v/v) ethanol in the pH 1.2 medium.
7. Pharmaceutical or nutraceutical composition, according to one or more of items 1 to 5, wherein the release in % of the pharmaceutical or nutraceutical active ingredient under in-vitro conditions in a pH 1.2 medium for 2 hours and subsequent change to a buffered medium pH 6.0 without the addition of calcium ions does not differ by more than plus/minus 20 (absolute percentage) in the same media but with the addition of 1.25 mM calcium ions in the pH 1.2 medium followed by pH 6.0 medium and optionally with the addition of 1.25 mM calcium ions ($Ca^{++}$) in the pH 1.2 medium and subsequent change to a buffered medium pH 6.0 with the addition of 1.25 mM calcium ions.
8. Pharmaceutical or nutraceutical composition according to one or more of items 1 to 7, wherein the release of the pharmaceutical or nutraceutical active under in-vitro conditions after 2 hours in pH 1.2 medium according to USP and subsequent change of the medium to buffered medium of pH 6.8 according to USP is 30 to 100% in a total time from 4 to 16 hours.
9. Pharmaceutical or nutraceutical composition according to one or more items 1 to 8, wherein the one or more water-insoluble polymers comprise (meth)acrylate copolymers
10. Pharmaceutical or nutraceutical composition according to one or more items 1 to 9, wherein the water-insoluble copolymer is a copolymer composed of free-radical polymerized units of more than 95 up to 100% by weight $C_1$- to $C_4$-alkyl esters of acrylic or of methacrylic acid and less than 5% by weight of acrylic or methacrylic acid.
11. Pharmaceutical or nutraceutical composition according to one or more items 1 to 10, wherein the one or more water-insoluble polymers belong to the group of vinyl polymers or copolymers or to the group of water-insoluble celluloses.
12. Pharmaceutical or nutraceutical composition according to one or more items 1 to 11, wherein the one or more water-soluble celluloses are selected from the group of methyl-, ethyl or propyl-ethers of cellulose or any combinations thereof.
13. Pharmaceutical or nutraceutical composition according items 12, wherein the one or more water-soluble celluloses are selected from the group of hydroxy-methyl-celluloses, hydroxy-ethyl-celluloses, hydroxy-propyl-celluloses, hydroxy-methyl-propyl-celluloses or sodium-carboxy-methyl-celluloses or any combinations thereof.
14. Pharmaceutical or nutraceutical composition according to one or more items 1 to 13, wherein outer coating is further comprising an emulsifier.
15. Pharmaceutical or nutraceutical composition according to one or more items 1 to 14, wherein the emusifier is a non-ionic emulsifier.
16. Pharmaceutical or nutraceutical composition according to item 15, wherein the emulsifier is a polyoxyethylene derivative of a sorbitan ester or a sorbitan ether.
17. Pharmaceutical or nutraceutical composition according to one or more items 1 to 16, wherein the outer coating comprises
    20 to 99, 20 to 90% by weight of the one or more water-insoluble polymers or copolymers,
    1 to 40, 2 to 20% by weight of the one or more water-soluble polymers, selected from the group of water soluble celluloses, polyvinyl pyrrolidones or polyethylene gylcols or any combinations thereof
    and optionally
    up to 20, 0 to 20, 0 to 15, 1 to 10% by weight of an emulsifier
    and optionally
    up to 60, 0-60, 5 to 50% by weight of pharmaceutical or nutraceutically acceptable
    excipients,
    wherein the components add up to 100%.
18. Process for producing the pharmaceutical or nutraceutical composition according to one or more items 1 to 17 by forming the core comprising the active ingredient by direct compression, compression of dry, wet or sintered granules, by extrusion and subsequent rounding off, by wet or dry granulation, by direct pelleting or by binding powders onto active ingredient-free beads or neutral cores or active ingredient-containing particles and by applying the inner coating layer and the outer coating layer in the form of aqueous dispersions or organic solutions in spray processes or by fluidized bed spray granulation.
19. Use of a pharmaceutical or nutraceutical composition according to one or more items 1 to 17 as a sustained release pharmaceutical or nutraceutical composition with resistance against the influence of ethanol and optionally with resistance against the influence of calcium ions.

EXAMPLES

Preparation of Core Caffeine Pellets

Drug Layering
Core used: Non pareil seeds (size 707-841 microns)
Quantity taken: 600.0 g
Formula:

| Ingredients | Manufacturer | Solid content (g) | Qty. batch (g) |
|---|---|---|---|
| Caffeine anhydrous | Aarti Drugs | 600 | 600 |
| Hydroxypropyl methyl cellulose (Pharmacoat 603) | Shin-Etsu | 85.5 | 85.5 |
| Yellow iron oxide | BASF | 3 | 3 |
| Water | | | 7917.75 |
| Total | | 688.5 | 8606.25 |

Total solid content: 8% w/w
Procedure for Drug Layering Suspension Preparation:
1. Caffeine was passed through sieve of 149 micron (100#)
2. Hydroxypropyl methyl cellulose was accurately weighed and dissolved in 7000 g water using an overhead stirrer.
3. Caffeine of step 1 was added to solution of step 2 under homogenization.
4. Homogenisation of step 2 was continued for 60 minutes.
5. Washing was given to the homogeniser with the remaining water and added to the final suspension.
6. The final prepared suspension was passed through a sieve of 420 microns (40#).
7. This suspension was further sprayed onto pellets in fluid bed processor.
8. After completion of spraying pellets were dried in fluid bed processor till the LOD was less than 2% w/w Equipment and in Process Coating Parameters:
Machine parameters: GPCG 3.1
Column height: 20-30 mm
Nozzle bore: 0.8 mm
Air flow mode: Auto
Inlet temp: 62-66° C.
Product temp: 38-43° C.
Atomisation Pressure: 1.0-1.1 bar
Spray rate: 17-31 gm/min
Silicon tube ID: 5 mm
Filter shaking mode: Asynchronous
Filter shaking: 5 sec
Filter shaking pause: 50 sec
Air flow: 130-142 m$^3$/h
Drug release of the uncoated pellets: 96% caffeine release obtained after 10 minutes in pH 6.8 buffer Preparation of Metoprolol Succinate Pellets
Preparation of Core (Extrusion Spheronisation Method)

| Ingredients | Manufacturer | Solid content (g) | Qty. batch (g) |
|---|---|---|---|
| Metoprolol Succinate | Poly Drugs | 1000 | 1000 |
| Microcrystalline cellulose (Avicel CL 611) | FMC Biopolymer | 600 | 600 |
| Microcrystalline cellulose (Avicel 101) | FMC Biopolymer | 400 | 400 |
| Water | | | 850 |
| Total | | 2000 | 2850 |

Procedure:
1. All the ingredients were sifted through 30# sieve.
2. Mixed together in RMG for 15 min.
3. Granulation was carried out in RMG.
Granulation

| Binder used: Water | Weight of binder used: 850 gm |
|---|---|
| Mixing Instrument used: RMG | Time used: 20 minutes |
| Granulator used: RMG | Total Granulation time: 21 minutes |

| Dry Mixing | | Binder Addition | | Wet Mixing | | Chopper Used | |
|---|---|---|---|---|---|---|---|
| Time | Speed | Time | Speed | Time | Speed | Time | Speed |
| 15 min | Slow | 2 min | Slow | 3 min | Slow | 1 min | 7 |

Extrusion Parameters:

| Extruder type: Cone | Type of screw rotation: single |
|---|---|
| Extruder screw: Single | Screw speed: 50 RPM |
| Extrusion pressure: 2.2-2.5 bar | Screen diameter: 1.0 mm |
| Extrusion temperature: 20-25° C. | Feed rate: 80-100 g/min |
| Extrusion time: 20 min | |

The extrudes were spheronised in 4 equal lots using the following parameters:

Spheronisation Parameters:
Spheronizer plate type: 2 mm
Spheronizer speed: 1800 RPM
Spheronisation time: 5 minutes After completion of spheronisation the pellets were dried in fluid bed processor till the LOD was less than 2% w/w Result:

Drug release of the uncoated pellets: 95% Metoprolol Succinate release obtained after 15 minutes in pH 6.8 buffer Preparation of Theophylline Pellets
Preparation of Core (Extrusion Spheronization Method)

| Ingredients | Manufacturer | Solid content (g) | Qty. batch (g) |
|---|---|---|---|
| Theophylline | Aarti Drugs Ltd. | 1000 | 1000 |
| Microcrystalline cellulose (Avicel CL 611) | FMC Biopolymer | 600 | 600 |
| Microcrystalline cellulose (Avicel 101) | FMC Biopolymer | 400 | 400 |
| Water | | | 1480 |
| Total | | 2000 | 3480 |

Note:
After sifting total blend of 2 kg was divided in 2 lots each of 1 kg.

Procedure:
1. All the ingredients were co-sifted through 40# sieve.
2. Mixed together in PLM for 15 min.
3. Granulation was carried out in PLM.

Granulation

| | |
|---|---|
| Binder used: Water | Weight of binder used: 730 gm |
| Mixing Instrument used: PLM | Time used: 18 minutes |
| Granulator used: PLM | Total Granulation time: 18 minutes |

| Dry Mixing | | Binder Addition | | Wet Mixing | |
|---|---|---|---|---|---|
| Time | Speed | Time | Speed | Time | Speed |
| 15 min | Minimum | 2 min | Minimum | 1 min | Minimum |

Extrusion Parameters:

| | |
|---|---|
| Extruder type: Cone | Type of screw rotation: single |
| Extruder screw: Single | Screw speed: 50 RPM |
| Extrusion pressure: 2.2 bar | Screen diameter: 1.0 mm |
| Extrusion temperature: 20-25° C. | Feed rate: 80-100 g/min |
| Extrusion time: 20 min | |

The extrudates were spheronised in 4 equal lots using the following parameters:

Spheronisation Parameters:
Spheronizer plate type: 2 mm
Spheronizer speed: 1800 RPM
Spheronisation time: 3 minutes 30 seconds After completion of spheronisation the pellets were dried in fluid bed processor till the LOD was less than 2% w/w Result:

Drug release of the uncoated pellets: 87% Theophylline release obtained after 45 minutes in pH 6.8 buffer.

Coating Process
Alginic Acid and Salts Used in Examples

| Commercial Name | Supplier | Viscosity Specification Sodium alginate | Calculated Viscosity for 1% solution comparative |
|---|---|---|---|
| Protanal CR 8133 (KELTONE ® LVCR) | FMC Biopolymers | 100-300 cP for 2% w/w solution | 50-150 cP for 1% w/w solution |

Analytical Methodology
1) Caffeine Pellets and Tablets
A) Dissolution Conditions
1) Dissolution Parameters
Apparatus: USP Type II
Dissolution Medium: Acid stage medium for 2 hrs followed by buffer stage medium (till 24 hours)
Volume of Medium: 900 mL for acid stage, 900 mL for buffer stage
Speed: 50 rpm
Temperature: 37° C.±0.5° C.
Withdrawal Volume: 10 ml
Sampling point: Acid stage—2 hour, Buffer stage—4, 6, 8, 12, 16, 20, 24 hours (hr)
2) Dissolution Mediums
I. Acid stage medium—0.1 N HCl pH 1.2 followed by buffer stage medium—pH 6.8 $PO_4$ buffer
II. Acid stage medium—ethanolic 0.1 N HCl (40% EtOH) followed by buffer stage medium—pH 6.8 $PO_4$ buffer
III. Acid stage medium—0.1 N HCl; Buffer stage medium—pH 6.0 PO4 buffer
IV. Acid stage medium—0.1 N HCl with 1.25 mM calcium ($Ca^{++}$) followed by buffer stage medium—pH 6.0 PO4 buffer with 1.25 mM $Ca^{++}$
V. Acid stage medium—0.1 N HCl with $Ca^{++}$ followed by buffer stage medium—pH 6.0 PO4 buffer (without $Ca^{++}$)
3) Composition of Dissolution Mediums
1) Buffer Stage Medium pH 6.8
6.8 g of Potassium dihydrogen phosphate was weighed and transferred to 1 liter beaker. To this, 500 mL water and 0.89 g of sodium hydroxide pellets were added and volume was made up to 1000 mL with water. The pH was adjusted to 6.8±0.05 using 2N NaOH or 2N HCl.
2) Buffers with Calcium
0.185 g of Calcium chloride di-hydrate was weighed and mixed with 1 liter buffer solutions.
4) Dissolution Procedure:
Acid Stage: Accurately weighed pellets or tablets of caffeine were transferred in six different dissolution jars and then the dissolution test was performed as per parameters given in the method above (Acid Stage). After 2 hr 10 mL of aliquot was removed and analyzed as acid stage sample solution.
Buffer Stage: The pellets or tablets after acid stage were transferred to buffer stage medium pH 6.8. The dissolution test was continued as per parameters given in the method above (Buffer Stage). The aliquots of each interval ware filtered through 0.45 μm nylon membrane syringe filter discarding first few mL of the filtrate and analyzed as buffer stage sample solution.
B) Chromatographic Conditions
Column: Agilent Zorbax Eclipse XDB C8 column, 150× 4.6 mm, 5 μm or equivalent
Mobile Phase: Water:Acetonitrile: (80:20)
Wavelength: 273 nm
Column Temp: 25° C.

Injection Volume: 10 μL
Flow rate: 1 mL/minute
Run time: 5 minutes

1. Metoprolol Succinate Pellets

A) Dissolution Conditions

1) Dissolution Parameters

Apparatus: USP Type II

Dissolution Medium: Acid stage medium for 2 hrs followed by buffer stage medium (22 hr)

Volume of Medium: 900 mL for acid stage, 500 mL for buffer stage

Speed: 50 rpm

Temperature: 37° C.±0.5° C.

Withdrawal: Volume 10 ml

2) Dissolution Mediums

I. Acid stage medium—0.1 N HCl; Buffer stage medium—pH 6.8 PO4 buffer
II. Acid stage medium—40% Alcoholic 0.1 N HCl; Buffer stage medium—pH 6.8 PO4 buffer
III. Acid stage medium—0.1 N HCl; Buffer stage medium—pH 6.0 PO4 buffer
IV. Acid stage medium—0.1 N HCl with 1.25 mM calcium ($Ca^{++}$) followed by buffer stage medium—pH 6.0 PO4 buffer with 1.25 mM $Ca^{++}$
V. Acid stage medium—0.1 N HCl with $Ca^{++}$ followed by buffer stage medium—pH 6.0 PO4 buffer (without $Ca^{++}$)

3) Composition of dissolution mediums

1) Buffer pH 6.8—

6.8 g of Potassium dihydrogen phosphate was weighed and transferred to 1 liter beaker. To this, 500 mL water and 0.89 g of sodium hydroxide pellets were added and volume was made up to 1000 mL with water. The pH was adjusted to 6.8+0.05 using 2N NaOH or 2N HCl.

2) Buffer pH 6.0—

6.8 g of Potassium dihydrogen phosphate was weighed and transferred to 1 liter beaker. To this, 500 mL water and 0.22 g of sodium hydroxide pellets were added and volume was made up to 1000 mL with water. The pH was adjusted to 6.0+0.05 using 2N NaOH or 2N HCl.

3) Buffers with Calcium—

0.185 g of Calcium chloride di-hydrate was weighed and mixed with 1 liter buffer solutions.

4) Dissolution Procedure:

Acid Stage: Accurately weighed pellets of metoprolol succinate were transferred in six different dissolution jars and then the dissolution test was performed as per parameters given in the method above (Acid Stage). After 2 hr 10 mL of aliquot was removed and analyzed as acid stage sample solution.

Buffer Stage: The pellets after acid stage were transferred to buffer stage medium pH 6.0 or 6.8. The dissolution test was continued as per parameters given in the method above (Buffer Stage). The aliquots of each interval ware filtered through 0.45 μm nylon membrane syringe filter discarding first few mL of the filtrate and analyzed as buffer stage sample solution.

B) Chromatographic Conditions

Column: Agilent Zorbax Eclipse XDB C8 column, 150× 4.6 mm, 5 μm or equivalent

Mobile Phase: Buffer:Acetonitrile: (75:25)

Wavelength: 280 nm

Column Temp: 30° C.

Injection Volume: 20 μL

Flow rate: 1 mL/minute

Preparation of Buffer for Mobile Phase:

9.0 gram of Sodium dihydrogen Phosphate was dissolved in 1000 ml of water, the pH of the solution was adjusted to 3.0 with orthophosphoric acid. The buffer was filtered through 0.45 μm nylon membrane filter.

2. Theophylline Pellets

A) Dissolution Conditions

1) Dissolution Parameters

Apparatus: USP Type II

Dissolution Medium: Acid stage medium for 2 hrs followed by buffer stage medium (22 hr)

Volume of Medium: 900 mL for acid stage, 900 mL for buffer stage

Speed: 50 rpm

Temperature: 37° C.±0.5° C.

Withdrawal Volume: 10 ml

2) Dissolution Mediums

I. Acid stage medium—0.1 N HCl; Buffer stage medium—pH 6.8 PO4 buffer
II. Acid stage medium—40% Alcoholic 0.1 N HCl; Buffer stage medium—pH 6.8 PO4 buffer
III. Acid stage medium—0.1 N HCl; Buffer stage medium—pH 6.0 PO4 buffer
IV. Acid stage medium—0.1 N HCl with 1.25 mM calcium ($Ca^{++}$) followed by buffer stage medium—pH 6.0 PO4 buffer with 1.25 mM $Ca^{++}$
V. Acid stage medium—0.1 N HCl with $Ca^{++}$ followed by buffer stage medium—pH 6.0 PO4 buffer (without $Ca^{++}$)

3) Composition of Dissolution Mediums

1) Buffer pH 6.8—

6.8 g of Potassium dihydrogen phosphate was weighed and transferred to 1 liter beaker. To this, 500 mL water and 0.89 g of sodium hydroxide pellets were added and volume was made up to 1000 mL with water. The pH was adjusted to 6.8+0.05 using 2N NaOH or 2N HCl.

2) Buffer pH 6.0—

6.8 g of Potassium dihydrogen phosphate was weighed and transferred to 1 liter beaker. To this, 500 mL water and 0.22 g of sodium hydroxide pellets were added and volume was made up to 1000 mL with water. The pH was adjusted to 6.0+0.05 using 2N NaOH or 2N HCl.

3) Buffers with Calcium—

0.185 g of Calcium chloride di-hydrate was weighed and mixed with 1 liter buffer solutions.

4) Dissolution Procedure:

Acid Stage: Accurately weighed pellets of Theophylline were transferred in six different dissolution jars and then the dissolution test was performed as per parameters given in the method above (Acid Stage). After 2 hr 10 mL of aliquot was removed and analyzed as acid stage sample solution.

Buffer Stage: The pellets after acid stage were transferred to buffer stage medium pH 6.8. The dissolution test was continued as per parameters given in the method above (Buffer Stage). The aliquots of each interval ware filtered through 0.45 μm nylon membrane syringe filter discarding first few mL of the filtrate and analyzed as buffer stage sample solution.

B) Chromatographic Conditions

Column: Agilent Zorbax Eclipse XDB C18 column, 150× 4.6 mm, 5 μm or equivalent

Mobile Phase: Water:Methanol:Glacial acetic acid (64:35:1)
Wavelength: 254 nm
Column Temp: 25° C.
Injection Volume: 10 μL
Flow rate: 1 mL/minute
General Acceptance Criteria
1) Less than +/−20% absolute deviation of drug release in the pH 1.2 medium (acid stage release) with 40% ethanol followed by buffered medium (buffer stage release) pH 6.8 without ethanol from the release values in the pH 1.2 medium without ethanol followed by the buffered medium pH 6.8 without ethanol.
2) Optionally: Less than +/−20% absolute deviation of drug release in the pH 1.2 medium with 1.25 mM $Ca^{++}$ followed by buffered medium pH 6.0 without $Ca^{++}$ from the release values in the pH 1.2 medium without $Ca^{++}$ followed by the buffered medium pH 6.0 without $Ca^{++}$ or optionally in the pH 1.2 medium with 1.25 mM $Ca^{++}$ followed by the buffered medium pH 6.0 with 1.25 mM $Ca^{++}$ Caffeine Pellets (Examples 1C-6C)

Example 1C (Comparative): Plain EUDRAGIT® NE 30D

Coating of 5% EUDRAGIT® NE 30D
Formula for 15% w/w Polymer Coating on 100 g Pellets

| Ingredient | Manufacturer | Quantity/Batch [g] | Solid content [g] |
|---|---|---|---|
| EUDRAGIT ® NE 30D | Evonik industries | 50 | 15 |
| Talc | Luzenac | 7.5 | 7.5 |
| Purified Water | | 92.5 | |
| Total | | 150 | 22.5 |

Solid content of coating suspension: 15% w/w
For 5% EUDRAGIT® NE 30D coating on 50 g pellets 25 g coating suspension sprayed Curing parameter: Drying at 50° C. for 24 hours in tray dryer
Procedure for Coating Suspension Preparation:
1. Talc was homogenized in water for 30 minutes.
2. EUDRAGIT® NE 30D was weighed accurately and kept for stirring using an overhead stirrer
3. Homogenized talc suspension was added to EUDRAGIT® NE 30D dispersion and stirring was continued for further 15 min.
4. The final prepared suspension was passed through a sieve of 250 microns (60#).
5. The final suspension was further sprayed onto pellets in fluid bed processor.
Equipment and in Process Coating Parameters for Pellets:
Instrument used: Huttlin Mycrolab
Silicone tube: 2.0 mm inner diameter
Nozzle bore: 0.8 mm
Air flow mode: Auto
Atomisation pressure: 0.9-1.0 bar
Inlet temperature: 23-26° C.
Product temperature: 22° C.-23° C.
Microclimate pressure: 0.5 bar
Spray rate: 0.4-0.8 g/min Results Example 1C

| API (Caffeine) Release [%] | | | | | | | | | |
|---|---|---|---|---|---|---|---|---|---|
| Acid stage Release | | Buffer stage Release | | | | | | | |
| Acid Medium pH 1.2 | 2 hr | Buffer Medium | 4 hr | 6 hr | 8 hr | 12 hr | 16 hr | 20 hr | 24 hr |
| 0.1 N HCl | 0 | pH 6.8 | 1 | 4 | 5 | 10 | 13 | 16 | 22 Fails |
| 40% EtOH HCl | 84 | pH 6.8 | 97 | 99 | 100 | 100 | 100 | 100 | 100 |

Example 2C (Comparative): Plain EUDRAGIT® NE 30D

Coating of 10% EUDRAGIT® NE 30D (by Weight Calculated to the Weight of the Core)
Coating Formula, procedure for coating suspension preparation, equipment and in-process Coating parameters for inner layer same as example 1C.
For 10% coating EUDRAGIT® NE 30D coating on 50 g pellets 50 g coating suspension sprayed Results Example 2C

| API (Caffeine) Release [%] | | | | | | | | | |
|---|---|---|---|---|---|---|---|---|---|
| Acid stage Release | | Buffer stage Release | | | | | | | |
| Acid Medium | 2 hr | Buffer Medium | 4 hr | 6 hr | 8 hr | 12 hr | 16 hr | 20 hr | 24 hr |
| 0.1 N HCl | 0 | pH 6.8 | 0 | 1 | 2 | 6 | 10 | 12 | 15 Fails |
| 40% EtOH HCl | 64 | pH 6.8 | 80 | 87 | 93 | 97 | 99 | 99 | 99 |

Example 3C (Comparative): Plain EUDRAGIT® NE 30D

Coating of 15% EUDRAGIT® NE 30D (by Weight Calculated to the Weight of the Core)

Coating Formula, procedure for coating suspension preparation, equipment and in-process coating parameters for inner layer same as example 1C.

For 15% coating EUDRAGIT® NE 30D coating on 50 g pellets 75 g coating suspension sprayed

Results Example 3C

| API (Caffeine) Release [%] | | | | | | | | | | |
|---|---|---|---|---|---|---|---|---|---|---|
| Acid stage Release | | | Buffer stage Release | | | | | | | |
| Acid Medium | 2 hr | Buffer Medium | 4 hr | 6 hr | 8 hr | 12 hr | 16 hr | 20 hr | 24 hr | |
| 0.1 N HCl | 0 | pH 6.8 | 0 | 0 | 1 | 5 | 7 | 9 | 11 | Fails |
| 40% EtOH HCl | 27 | pH 6.8 | 38 | 44 | 50 | 66 | 80 | 88 | 93 | |

Example 4C (Comparative): Bilayer Coating

Inner layer: Sodium Alginate (100-300 cP for 2% w/w solution)
Outer layer: EUDRAGIT® NE 30 D
Inner layer: 10% Sodium Alginate
Outer layer: 10% EUDRAGIT® NE 30 D
Ratio (w/w) Polymer Inner Layer:Polymer Outer Layer: 1:1

Inner Layer
Coating of 10% Sodium Alginate (by Weight Calculated to the Weight of the Core)
Formula for 20% w/w Polymer Coating on 400 g Pellets

| Ingredient | Manufacturer | Quantity/Batch [g] | Solid content [g] |
|---|---|---|---|
| Protanal CR 8133 (KELTONE ® LVCR) | FMC Biopolymers | 80 | 80 |
| Talc | Luzenac | 40 | 40 |
| Purified Water | | 2880 | |
| Total | | 3000 | 120 |

Solid Content of Coating Suspension: 4% w/w
For 10% KELTONE® LVCR coating on 400 g pellets 1500 g coating suspension sprayed
Procedure for Coating Suspension Preparation:
1. Sodium Alginate was weighed and kept under stirring with water for 60 minutes on an overhead stirrer to prepare 4% solution.
2. Talc was homogenized with remaining amount of water for 30 minutes.
3. Homogenized talc suspension was added to Alginate solution and stirring was continued for further 30 min.
4. The final prepared suspension was passed through a sieve of 420 microns (40#).
5. This suspension was further sprayed onto pellets in fluid bed processor.

Equipment and in Process Coating Parameters for Pellets:
Instrument used: GPCG 1.1
Silicone tube: 3.0 mm inner diameter
Column height: 20-40 mm
Nozzle bore: 0.8 mm
Filter shaking mode: Asynchronous
Filter shaking: 4 sec
Filter shaking pause: 50 sec
Air flow mode: Auto
Air flow: 70-84 CFM
Atomisation pressure: 1.2-1.4 bar
Inlet temperature: 61-65° C.
Product temperature: 47° C.-56° C.
Spray rate: 4-13.5 g/min Outer Layer: Coating of 10% EUDRAGIT® NE 30 D (by Weight Calculated to the Weight of the Core)

Coating Formula, procedure for coating suspension preparation, equipment and in-process coating parameters for inner layer same as example 1C.

Curing Parameter:
Drying at 50° C. for 24 hours in tray dryer

Results Example 4C

| API (Caffeine) Release [%] | | | | | | | | | | |
|---|---|---|---|---|---|---|---|---|---|---|
| Acid stage Release | | | Buffer stage Release | | | | | | | |
| Acid Medium | 2 hr | Buffer Medium | 4 hr | 6 hr | 8 hr | 12 hr | 16 hr | 20 hr | 24 hr | |
| 0.1 N HCl | 0 | pH 6.8 | 0 | 2 | 15 | 44 | 63 | 77 | 87 | Fails |
| 40% EtOH HCl | 33 | pH 6.8 | 98 | 99 | 99 | 99 | — | — | — | |

Example 5C (Comparative): Bilayer Coating

Inner layer: Sodium Alginate (100-300 cP for 2% w/w solution)
Outer layer: EUDRAGIT® NE 30 D
Inner layer: 20% Sodium Alginate (% by weight calculated to the weight of the core)
Outer layer: 10% EUDRAGIT® NE 30 D (solid content, % by weight calculated to the weight of the core)
Ratio (Dry w/w) Sodium Alginate:EUDRAGIT® NE=2:1

Inner Layer

Coating of 20% Sodium Alginate

Coating Formula, procedure for coating suspension preparation, equipment and in process coating parameters for inner layer same as example 4C.

For 20% KELTONE® LVCR coating on 400 g pellets 3000 g coating suspension sprayed Outer Layer:

EUDRAGIT® NE 30 D Coating

Coating of 10% EUDRAGIT® NE 30 D

Coating Formula, procedure for coating suspension, preparation, equipment and in process coating parameters for inner layer same as example 1C.

Curing Parameter:

Drying at 50° C. for 24 hours in tray dryer

Results Example 5C

| | API (Caffeine) Release [%] | | | | | | | | |
|---|---|---|---|---|---|---|---|---|---|
| Acid stage Release | | Buffer stage Release | | | | | | | |
| Acid Medium | 2 hr | Buffer Medium | 4 hr | 6 hr | 8 hr | 12 hr | 16 hr | 20 hr | 24 hr |
| 0.1 N HCl | 0 | pH 6.8 | 0 | 1 | 22 | 66 | 84 | 93 | 98 Fails |
| 40% EtOH HCl | 6 | pH 6.8 | 41 | 64 | 78 | 90 | 94 | 96 | 99 |

Example 6C (Comparative): Bilayer Coating

Inner layer: Sodium Alginate (100-300 cP for 2% w/w solution)

Outer layer: EUDRAGIT® NE 30 D

Inner layer: 20% Sodium Alginate (% by weight calculated to the weight of the core)

Outer layer: 15% EUDRAGIT® NE 30 D (solid content, % by weight calculated to the weight of the core)

Ratio (Dry w/w) Sodium Alginate:EUDRAGIT® NE=1.3:1

Inner Layer

Coating of 20% Sodium Alginate

Coating Formula, procedure for coating suspension preparation, equipment and in-process coating parameters for inner layer same as example 4C.

For 20% KELTONE® LVCR coating on 400 g pellets 3000 g coating suspension sprayed Outer Layer EUDRAGIT® NE 30 D Coating Coating of 15% EUDRAGIT® NE 30 D Coating Formula, procedure for coating suspension preparation, equipment and in-process coating parameters for inner layer same as example 1C.

Curing parameter: Drying at 50° C. for 24 hours in tray dryer

Results Example 6C

| | API (Caffeine) Release [%] | | | | | | | | |
|---|---|---|---|---|---|---|---|---|---|
| Acid stage Release | | Buffer stage Release | | | | | | | |
| Acid Medium | 2 hr | Buffer Medium | 4 hr | 6 hr | 8 hr | 12 hr | 16 hr | 20 hr | 24 hr |
| 0.1 N HCl | 0 | pH 6.8 | 0 | 0 | 0 | 10 | 28 | 50 | 67 Fails |
| 40% EtOH HCl | 1 | pH 6.8 | 2 | 3 | 4 | 6 | 10 | 23 | 44 |

Example 7C (Comparative): Bilayer Coating with Pore Former in Outer Coat

Inner coat: Sodium alginate 20% (% by weight calculated to the weight of the core) Outer coat:

35% by weight EUDRAGIT® NE 30 D (solid content) (calculated to the weight of the core)

HPC-LM 20% (calculated to the weight of EUDRAGIT® NE 30 D)

Ratio (Dry w/w) Sodium Alginate:EUDRAGIT® NE=0.57:1

Inner Layer

Core: Metoprolol succinate Pellets (18/20# Retained)

Coating of 20% Sodium alginate

Formula for 40% w/w Polymer Coating on 400 g Pellets

40% Coating on 400 g requires 6000 g total suspension.
20% Coating on 400 g requires 3000 g total suspension.

As Per Example 8

Procedure & Equipment and in Process Coating Parameters for Pellets as Per Example 8

Outer Layer

Coating of 35% EUDRAGIT® NE 30 D+HPC-LM 20%

Formula for 35% w/w Polymer Coating on 350 g Pellets

| Ingredient | Manufacturer | Solid Content [g] | Quantity/ Batch [g] |
|---|---|---|---|
| EUDRAGIT ® NE 30 D | Evonik industries | 122.5 | 408.33 |
| Talc (50%) | Luzenac | 61.25 | 61.25 |
| HPC-LM (20%) | NIPPON SODA CO., LTD | 24.5 | 24.5 |
| Purified Water | | | 894.25 |
| Total | | 208.25 | 1388.33 |

Solid Content of Coating Suspension: 15% w/w

Procedure for Coating Suspension Preparation:

1. HPC-LM was dissolved in 300 g water using overhead stirrer.

2. Then it was added to EUDRAGIT® NE 30 D dispersion slowly while stirring with overhead stirrer.
3. Talc was homogenized in remaining water for 30 minutes and then added to STEP 2 solution.
4. Resulted suspension was mixed for 15 minutes using overhead stirrer and then passed through 250 micron sieve and used for coating.

Equipment and in Process Coating Parameters for Pellets:
Instrument used: Pam Glatt GPCG 1.1
Silicone tube: 3.0 mm inner diameter
Column height: 15-20 mm
Nozzle bore: 0.8 mm
Filter shaking mode: Asynchronous
Filter shaking: 5 sec
Filter shaking pause: 250 sec
Air flow mode: Auto
Air flow: 80-91 CFM
Atomisation pressure: 1.1 bar
Inlet temperature: 28° C.-30° C.
Product temperature: 23° C.-24° C.
Spray rate: 3-5 g/min
Curing: 50° C. for 24 hr in Tray Dryer Results Example 7C

| API (Metoprolol succinate) Release [%] | | | | | | | | | |
|---|---|---|---|---|---|---|---|---|---|
| Acid stage Release | | Buffer stage Release | | | | | | | |
| Acid Medium | 2 hr | Buffer Medium | 4 hr | 6 hr | 8 hr | 12 hr | 16 hr | 20 hr | 24 hr |
| 0.1 N HCl | 0 | pH 6.8 | 10 | 53 | 91 | 100 | 100 | 100 | 100 Fails |
| 40% EtOH HCl | 1 | pH 6.8 | 3 | 8 | 21 | 66 | 93 | 96 | 96 |

Example 8: (Inventive) Bilayer Coating with Pore Former & Emulsifier in Outer Coat Inner coat: Sodium alginate 30% (% by weight calculated to the weight of the core)
Outer Coat:
25% by weight EUDRAGIT® NE 30 D (solid content) (calculated to the weight of the core)
hydroxyl-propyl-cellulose (HPC-LM) 8%
Tween® 80 10% (by weight calculated to the weight of EUDRAGIT® NE 30 D)
Ratio (Dry w/w) Sodium Alginate:EUDRAGIT® NE=1.2:1
Inner Layer
Core: Metoprolol succinate Pellets (18/20# retained)
Coating of 30% Sodium alginate
Formula for 40% w/w Polymer Coating on 400 g Pellets

| Ingredient | Manufacturer | Solid Content [g] | Quantity/ Batch [g] |
|---|---|---|---|
| Protanal CR 8133 (KELTONE® LVCR) | FMC Biopolymers | 160 | 160 |
| Talc | Luzenac | 80 | 80 |
| Purified Water | | | 5760 |
| Total | | 240 | 6000 |

Solid content of coating suspension: 4% w/w
40% Coating on 400 g requires 6000 g total suspension.
30% Coating on 400 g requires 4500 g total suspension.

Procedure for Coating Suspension Preparation:
1. Dissolve sodium alginate in 85% water to prepare a solution using an overhead stirrer for 1 hr.
2. Homogenize talc in remaining amount of water for 30 minutes.
3. Add talc suspension to Alginate solution and stir for further 30 minutes.
4. Filter final coating suspension through 420 micron sieve before spraying.

Equipment and in Process Coating Parameters for Pellets:
Instrument used: Pam Glatt GPCG 1.1
Silicone tube: 3.0 mm inner diameter
Column height: 15-20 mm
Nozzle bore: 0.8 mm
Filter shaking mode: Asynchronous
Filter shaking: 4 sec
Filter shaking pause: 100 sec
Air flow mode: Auto
Air flow: 70-85 CFM
Atomisation pressure: 1.4 bar
Inlet temperature: 70-83° C.
Product temperature: 51° C.-54° C.
Spray rate: 8-17 g/min Outer Layer
Coating of 25% EUDRAGIT® NE 30 D+(HPC-LM 8%+10% Tween® 80)
Formula for 25% w/w Polymer Coating on 400 g Pellets

| Ingredient | Manufacturer | Solid Content [g] | Quantity/ Batch [g] |
|---|---|---|---|
| EUDRAGIT® NE 30 D | Evonik industries | 100 | 333.33 |
| Talc (50%) | Luzenac | 50 | 50 |
| HPC-LM (8%) | NIPPON SODA CO., LTD | 8 | 8 |
| Tween 80 (10%) | Merck | 10 | 10 |
| Purified Water | | | 718.67 |
| Total | | 168 | 1120 |

Solid Content of Coating Suspension: 15% w/w
Procedure for Coating Suspension Preparation:
1. HPC-LM was dissolved in 150 g water using overhead stirrer.
2. Then it was added to EUDRAGIT® NE 30 D dispersion slowly while stirring with overhead stirrer.
3. Tween 80 was dissolved in 50 gm hot water.
4. Talc and tween 80 was homogenized in remaining water for 30 minutes and then added to STEP 2 solution.
5. Resulted suspension was mixed for 15 minutes using overhead stirrer and then passed through 250 micron sieve and used for coating.

Equipment and in Process Coating Parameters for Pellets:
Instrument used: Pam Glatt GPCG 1.1
Silicone tube: 3.0 mm inner diameter
Column height: 15-20 mm
Nozzle bore: 0.8 mm
Filter shaking mode: Asynchronous
Filter shaking: 5 sec
Filter shaking pause: 250 sec
Air flow mode: Auto
Air flow: 85-110 CFM
Atomisation pressure: 1.0-1.2 bar
Inlet temperature: 28° C.-35° C.
Product temperature: 24° C.-27° C.
Spray rate: 2-10 g/min
Curing: 50° C. for 24 hr in Tray Dryer Results Example 8

| API (Metoprolol succinate) Release [%] | | | | | | | | | |
|---|---|---|---|---|---|---|---|---|---|
| Acid stage Release | | Buffer stage Release | | | | | | | |
| Acid Medium | 2 hr | Buffer Medium | 4 hr | 6 hr | 8 hr | 12 hr | 16 hr | 20 hr | 24 hr |
| 0.1 N HCl | 5 | pH 6.8 | 26 | 43 | 54 | 67 | 75 | 82 | 87 | Passes
| 40% EtOH HCl | 16 | pH 6.8 | 45 | 62 | 71 | 81 | 88 | 93 | 96 |
| 0.1 N HCl | 5 | pH 6.0 | 28 | 46 | 58 | 72 | 80 | 87 | 93 |
| 0.1 N HCl + Ca$^{++}$ | 5 | pH 6.0 + Ca$^{++}$ | 27 | 46 | 58 | 72 | 81 | 88 | 92 |
| 0.1 N HCl + Ca$^{++}$ | 4 | pH 6.0 | 25 | 43 | 54 | 69 | 78 | 86 | 91 |

Example 9: (Inventive) Bilayer Coating with Pore Former & Emulsifier in Outer Coat Inner coat: Sodium alginate 30% (% by weight calculated to the weight of the core)

Outer Coat:

25% by weight EUDRAGIT® NE 30 D (solid content) calculated to the weight of the core HPC-LM 8%+10% Tween® 20 (by weight calculated to the weight of EUDRAGIT® NE 30 D (solid content)

Ratio (Dry w/w) Sodium Alginate:EUDRAGIT® NE=1.2:1

Inner Layer

Core: Metoprolol succinate Pellets (18/20# Retained)

Coating of 30% Sodium alginate

Formula for 40% w/w Polymer Coating on 400 g Pellets as Per Example 8

40% Coating on 400 g requires 6000 g total suspension.

30% Coating on 400 g requires 4500 g total suspension.

Procedure & Equipment and in Process Coating Parameters for Pellets as Per Example 1

Outer Layer

Coating of 25% EUDRAGIT® NE 30 D+(HPC-LM 8%+Tween 10%)

Formula for 25% w/w Polymer Coating on 400 g Pellets

| Ingredient | Manufacturer | Solid Content [g] | Quantity/Batch [g] |
|---|---|---|---|
| EUDRAGIT ® NE 30 D | Evonik industries | 100 | 333.33 |
| Talc (50%) | Luzenac | 50 | 50 |
| HPC-LM (8%) | NIPPON SODA CO., LTD | 8 | 8 |
| Tween 20 (10%) | Merck | 10 | 10 |
| Purified Water | | | 718.67 |
| Total | | 168 | 1120 |

Solid Content of Coating Suspension: 15% w/w

Procedure for Coating Suspension Preparation:

1. HPC-LM was dissolved in 150 g water using overhead stirrer.
2. Then it was added to EUDRAGIT® NE 30 D dispersion slowly while stirring with overhead stirrer.
3. Tween 80 was dissolved in 50 gm hot water.
4. Talc and tween 80 was homogenized in remaining water for 30 minutes and then added to STEP 2 solution.
5. Resulted suspension was mixed for 15 minutes using overhead stirrer and then passed through 250 micron sieve and used for coating.

Equipment and in Process Coating Parameters for Pellets:

Instrument used: Pam Glatt GPCG 1.1

Silicone tube: 3.0 mm inner diameter

Column height: 20 mm

Nozzle bore: 0.8 mm

Filter shaking mode: Asynchronous

Filter shaking: 5 sec

Filter shaking pause: 250 sec

Air flow mode: Auto

Air flow: 80-100 CFM

Atomisation pressure: 1.0 bar

Inlet temperature: 28° C.-30° C.

Product temperature: 24° C.-25° C.

Spray rate: 4-9 g/min

Curing: 50° C. for 24 hr in Tray Dryer

Results Example 9

| Acid stage Release | | Buffer stage Release | | | | | | | | |
|---|---|---|---|---|---|---|---|---|---|---|
| Acid Medium | 2 hr | Buffer Medium | 4 hr | 6 hr | 8 hr | 12 hr | 16 hr | 20 hr | 24 hr | |
| 0.1 N HCl | 1 | pH 6.8 | 9 | 27 | 46 | 71 | 84 | 93 | 98 | Passes |
| 40% EtOH HCl | 4 | pH 6.8 | 21 | 43 | 61 | 81 | 92 | 97 | 99 | |
| 0.1 N HCl | 0 | pH 6.0 | 6 | 21 | 38 | 65 | 79 | 90 | 97 | |
| 0.1 N HCl + $Ca^{++}$ | 0 | pH 6.0 + $Ca^{++}$ | 8 | 25 | 43 | 69 | 83 | 92 | 98 | |
| 0.1 N HCl + $Ca^{++}$ | 0 | pH 6.0 | 7 | 23 | 39 | 65 | 81 | 91 | 97 | |

Example 10: (Inventive) Bilayer Coating with Pore Former & Emulsifier in Outer Coat Inner coat: Sodium alginate 20% (% by weight calculated to the weight of the core)
Outer Coat:
25% by weight EUDRAGIT® NE 30 D (solid content) calculated to the weight of the core
HPC-LM 15%+Tween® 80 10% (by weight calculated to the weight of EUDRAGIT® NE 30 D (solid content))
Ratio (Dry w/w) Sodium Alginate:EUDRAGIT® NE=0.8:1
Inner Layer
Core: Metoprolol succinate Pellets (18/20# retained)
Coating of 20% Sodium alginate
Formula for 40% w/w Polymer Coating on 400 g Pellets as Per Example 8
40% Coating on 400 g requires 6000 g total suspension.
20% Coating on 400 g requires 3000 g total suspension.
Procedure & Equipment and in Process Coating Parameters for Pellets as Per Example 1
Outer Layer
Coating of 25% EUDRAGIT® NE 30 D+HPC-LM 15%+Tween 80 10%
Formula for 25% w/w Polymer Coating on 350 g Pellets

| Ingredient | Manufacturer | Solid Content [g] | Quantity/Batch [g] |
|---|---|---|---|
| EUDRAGIT® NE 30 D | Evonik Industries AG | 87.5 | 291.66 |
| Talc (100%) | Luzenac | 87.5 | 87.5 |
| HPC-LM (15%) | NIPPON SODA CO., LTD | 13.125 | 13.125 |
| Tween 80 (10%) | Merck | 8.75 | 8.75 |
| Purified Water | | | 911.465 |
| Total | | 196.875 | 1312.5 |

Solid Content of Coating Suspension: 15% w/w
Procedure for Coating Suspension Preparation:
1. HPC-LM was dissolved in 300 g water using overhead stirrer.
2. Then it was added to EUDRAGIT® NE 30 D dispersion slowly while stirring with overhead stirrer.
3. Tween 80 was dissolved in 50 gm hot water.
4. Talc and tween 80 was homogenized in remaining water for 30 minutes and then added to STEP 2 solution.
5. Resulted suspension was mixed for 15 minutes using overhead stirrer and then passed through 250 micron sieve and used for coating.

Equipment and in Process Coating Parameters for Pellets:
Instrument used: Pam Glatt GPCG 1.1
Silicone tube: 3.0 mm inner diameter
Column height: 15-20 mm
Nozzle bore: 0.8 mm
Filter shaking mode: Asynchronous
Filter shaking: 5 sec
Filter shaking pause: 250 sec
Air flow mode: Auto
Air flow: 80-90 CFM
Atomisation pressure: 1.0 bar
Inlet temperature: 28° C.-30° C.
Product temperature: 24° C.-25° C.
Spray rate: 4-5 g/min
Curing: 50° C. for 24 hr in Tray Dryer Results Example 10

| Acid stage Release | | Buffer stage Release | | | | | | | | |
|---|---|---|---|---|---|---|---|---|---|---|
| Acid Medium | 2 hr | Buffer Medium | 4 hr | 6 hr | 8 hr | 12 hr | 16 hr | 20 hr | 24 hr | |
| 0.1 N HCl | 14 | pH 6.8 | 30 | 71 | 95 | 99 | 99 | 100 | 100 | Passes |
| 40% EtOH HCl | 11 | pH 6.8 | 38 | 77 | 94 | 98 | 99 | 99 | 99 | |
| 0.1 N HCl | 13 | pH 6.0 | 29 | 75 | 97 | 100 | 100 | 99 | 100 | |
| 0.1 N HCl + $Ca^{++}$ | 13 | pH 6.0 + $Ca^{++}$ | 29 | 75 | 97 | 99 | 99 | 100 | 100 | |
| 0.1 N HCl + $Ca^{++}$ | 14 | pH 6.0 | 31 | 75 | 96 | 99 | 99 | 100 | 100 | |

Example 11: (Inventive) Bilayer Coating with Pore Former & Emulsifier in Outer Coat Inner coat: Sodium alginate 20% (% by weight calculated to the weight of the core)
Outer Coat:
30% by weight EUDRAGIT® NE 30 D (solid content) calculated to the weight of the core
HPC-LM 15%+Tween® 10% (by weight calculated to the weight of EUDRAGIT® NE 30 D)
Ratio (Dry w/w) Sodium Alginate:EUDRAGIT® NE=0.66:1
Inner Layer
Core: Metoprolol succinate Pellets (18/20# Retained)
Coating of 20% Sodium alginate Equipment and in Process Coating Parameters for Pellets:
Instrument used: Pam Glatt GPCG 1.1
Silicone tube: 3.0 mm inner diameter
Column height: 15-20 mm
Nozzle bore: 0.8 mm
Filter shaking mode: Asynchronous
Filter shaking: 5 sec
Filter shaking pause: 250 sec
Air flow mode: Auto
Air flow: 80-90 CFM
Atomisation pressure: 1.0 bar
Inlet temperature: 28° C.-30° C.
Product temperature: 24° C.-25° C.
Spray rate: 4-5 g/min
Curing: 50° C. for 24 hr in Tray Dryer
Result:

| | | API (Metoprolol succinate) Release [%] | | | | | | | | |
|---|---|---|---|---|---|---|---|---|---|---|
| Acid stage Release | | | Buffer stage Release | | | | | | | |
| Acid Medium | 2 hr | Buffer Medium | 4 hr | 6 hr | 8 hr | 12 hr | 16 hr | 20 hr | 24 hr | |
| 0.1 N HCl | 4 | pH 6.8 | 18 | 49 | 86 | 99 | 100 | 100 | 100 | Passes |
| 40% EtOH HCl | 7 | pH 6.8 | 26 | 61 | 89 | 99 | 100 | 100 | 100 | |
| 0.1 N HCl | 6 | pH 6.0 | 20 | 49 | 85 | 99 | 99 | 99 | 99 | |
| 0.1 N HCl + $Ca^{++}$ | 5 | pH 6.0 + $Ca^{++}$ | 21 | 49 | 85 | 99 | 99 | 100 | 100 | |
| 0.1 N HCl + $Ca^{++}$ | 5 | pH 6.0 | 20 | 49 | 84 | 99 | 99 | 99 | 99 | |

Formula for 40% w/w Polymer Coating on 400 g Pellets as Per Example 8
40% Coating on 400 g requires 6000 g total suspension.
20% Coating on 400 g requires 3000 g total suspension.
Procedure & Equipment and in Process Coating Parameters for Pellets as Per Example 1
Outer Layer
Coating of 30% EUDRAGIT® NE 30 D+HPC-LM 15%+Tween 80 (10% solution)
Formula for 30% w/w Polymer Coating on 350 g Pellets

| Ingredient | Manufacturer | Solid Content [g] | Quantity/ Batch [g] |
|---|---|---|---|
| EUDRAGIT® NE 30 D | Evonik industries | 105 | 350 |
| Talc (100%) | Luzenac | 105 | 105 |
| HPC-LM (15%) | NIPPON SODA CO., LTD | 15.75 | 15.75 |
| Tween 80 (10%) | Merck | 10.5 | 10.5 |
| Purified Water | | | 1093.75 |
| Total | | 236.25 | 1575 |

Solid Content of Coating Suspension: 15% w/w
Procedure for Coating Suspension Preparation:
1. HPC-LM was dissolved in 300 g water using overhead stirrer.
2. Then it was added to EUDRAGIT® NE 30 D dispersion slowly while stirring with overhead stirrer.
3. Tween 80 was dissolved in 50 gm hot water.
4. Talc and tween 80 was homogenized in remaining water for 30 minutes and then added to STEP 2 solution.
5. Resulted suspension was mixed for 15 minutes using overhead stirrer and then passed through 250 micron sieve and used for coating.

Example 12: (Inventive) Bilayer Coating with Pore Former & Emulsifier in Outer Coat Inner coat: Sodium alginate 20% (% by weight calculated to the weight of the core)
Outer Coat:
20% by weight EUDRAGIT® NE 30 D (solid content) calculated to the weight of the core
HPC-LM 15%+Tween® 10% (by weight calculated to the weight of EUDRAGIT® NE 30 D)
Ratio (Solid w/w) Sodium Alginate:EUDRAGIT® NE=1:1
Inner Layer
Core: Theophylline Pellets (18/20# Retained)
Coating of 20% Sodium alginate
Formula for 40% w/w Polymer Coating on 400 g Pellets as Per Example 8
40% Coating on 400 g requires 6000 g total suspension.
20% Coating on 400 g requires 3000 g total suspension.
Procedure & Equipment and in Process Coating Parameters for Pellets as Per Example 1
Outer Layer
Coating of 20% EUDRAGIT® NE 30 D+HPC-LM 15%+10% Tween 80
Formula for 20% w/w Polymer Coating on 350 g Pellets

| Ingredient | Manufacturer | Solid Content [g] | Quantity/ Batch [g] |
|---|---|---|---|
| EUDRAGIT® NE 30 D | Evonik industries | 70 | 233.33 |
| Talc (100%) | Luzenac | 70 | 70 |
| HPC-LM (15%) | NIPPON SODA CO., LTD | 10.5 | 10.5 |

-continued

| Ingredient | Manufacturer | Solid Content [g] | Quantity/Batch [g] |
|---|---|---|---|
| Tween 80 (10%) | Merck | 7 | 7 |
| Purified Water | | | 554.17 |
| Total | | 157.5 | 875 |

Solid Content of Coating Suspension: 18% w/w
Procedure for Coating Suspension Preparation:
1. HPC-LM was dissolved in 150 g water using overhead stirrer.
2. Then it was added to EUDRAGIT® NE 30 D dispersion slowly while stirring with overhead stirrer.
3. Tween 80 was dissolved in 50 gm hot water.
4. Talc and tween 80 was homogenized in remaining water for 30 minutes and then added to STEP 2 solution.
5. Resulted suspension was mixed for 15 minutes using overhead stirrer and then passed through 250 micron sieve and used for coating.

Equipment and in Process Coating Parameters for Pellets:
Instrument used: Pam Glatt GPCG 1.1
Silicone tube: 3.0 mm inner diameter
Column height: 15-20 mm
Nozzle bore: 0.8 mm
Filter shaking mode: Asynchronous
Filter shaking: 5 sec
Filter shaking pause: 250 sec
Air flow mode: Auto
Air flow: 80-90 CFM
Atomisation pressure: 1.1 bar
Inlet temperature: 27° C.-31° C.
Product temperature: 24° C.-25° C.
Spray rate: 2-8 g/min
Curing: 50° C. for 24 hr in Tray Dryer Results Example 12

| API (Theophylline) Release [%] | | | | | | | | | |
|---|---|---|---|---|---|---|---|---|---|
| Acid stage Release | | Buffer stage Release | | | | | | | |
| Acid Medium | 2 hr | Buffer Medium | 4 hr | 6 hr | 8 hr | 12 hr | 16 hr | 20 hr | 24 hr |
| 0.1 N HCl | 0 | pH 6.8 | 5 | 36 | 68 | 97 | 102 | 102 | 100 Passes |
| 40% EtOH HCl | 1 | pH 6.8 | 13 | 48 | 79 | 99 | 100 | 100 | 100 |
| 0.1 N HCl | 1 | pH 6.0 | 6 | 44 | 75 | 97 | 99 | 99 | 99 |
| 0.1 N HCl + Ca$^{++}$ | 0 | pH 6.0 + Ca$^{++}$ | 5 | 51 | 93 | 101 | 100 | 100 | 100 |
| 0.1 N HCl + Ca$^{++}$ | 0 | pH 6.0 | 7 | 46 | 76 | 96 | 99 | 100 | 100 |

Example 13: (Inventive) Bilayer Coating with Pore Former in Outer Coat

Inner coat: Sodium alginate 30% (by weight calculated to the weight of the core)
Outer Coat:
EUDRAGIT® NE 30 D 15% by weight (solid content) calculated to the weight of the core
HPC-LM 8% (by weight calculated to the weight of EUDRAGIT® NE 30 D)
Ratio (Solid w/w) Sodium Alginate:EUDRAGIT® NE=2:1

Inner Layer
Core: Metoprolol succinate Pellets (18/20# Retained)
Coating of 30% Sodium alginate
Formula for 40% w/w Polymer Coating on 400 g Pellets as Per Example 8
40% Coating on 400 g requires 6000 g total suspension.
30% Coating on 400 g requires 4500 g total suspension.
Procedure & Equipment and in Process Coating Parameters for Pellets as Per Example 1
Outer Layer
Coating of 15% EUDRAGIT® NE 30 D+HPC-LM 8%
Formula for 15% w/w Polymer Coating on 400 g Pellets

| Ingredient | Manufacturer | Solid Content [g] | Quantity/Batch [g] |
|---|---|---|---|
| EUDRAGIT ® NE 30 D | Evonik industries | 60 | 200 |
| Talc (50%) | Luzenac | 30 | 30 |
| HPC-LM (8%) | NIPPON SODA CO., LTD | 4.8 | 4.8 |
| Purified Water | | | 397.2 |
| Total | | 94.8 | 632 |

Solid Content of Coating Suspension: 15% w/w
Procedure for Coating Suspension Preparation:
1. HPC-LM was dissolved in 100 g water using overhead stirrer.
2. Then it was added to EUDRAGIT® NE 30 D dispersion slowly while stirring with overhead stirrer.
3. Talc was homogenized in remaining water for 30 minutes and then added to STEP 2 solution.
4. Resulted suspension was mixed for 15 minutes using overhead stirrer and then passed through 250 micron sieve and used for coating.

Equipment and in Process Coating Parameters for Pellets:
Instrument used: Pam Glatt GPCG 1.1
Silicone tube: 3.0 mm inner diameter
Column height: 20 mm
Nozzle bore: 0.8 mm
Filter shaking mode: Asynchronous
Filter shaking: 5 sec
Filter shaking pause: 250 sec
Air flow mode: Auto
Air flow: 80-90 CFM
Atomisation pressure: 1.0 bar
Inlet temperature: 27° C.-28° C.
Product temperature: 24° C.-25° C.
Spray rate: 4-5 g/min
Curing: 50° C. for 24 hr in Tray Dryer Results Example 13

| API (Metoprolol succinate) Release [%] | | | | | | | | | | |
|---|---|---|---|---|---|---|---|---|---|---|
| Acid stage Release | | Buffer stage Release | | | | | | | | |
| Acid Medium | 2 hr | Buffer Medium | 4 hr | 6 hr | 8 hr | 12 hr | 16 hr | 20 hr | 24 hr | |
| 0.1 N HCl | 10 | pH 6.8 | 12 | 12 | 13 | 37 | 93 | 95 | 100 | Passes |
| 40% EtOH HCl | 11 | pH 6.8 | 14 | 14 | 15 | 52 | 95 | 100 | 100 | |

Example 14: (Inventive) Bilayer Coating with Pore Former in Outer Coat

Inner coat: Sodium alginate 40% (by weight calculated to the weight of the core)

Outer Coat:

20% by weight EUDRAGIT® NE 30 D (solid content) calculated to the weight of the core HPC-LM 4% (by weight calculated to the weight of EUDRAGIT® NE 30 D)

Ratio (Solid w/w) Sodium Alginate:EUDRAGIT® NE=2:1

Inner Layer

Core: Metoprolol succinate Pellets (18/20# Retained)

Coating of 40% Sodium alginate

Formula for 40% w/w Sodium Alginate Coating on 400 g Pellets as Per Example 8

Procedure & Equipment and in Process Coating Parameters for Pellets as Per Example 1

2. Then it was added to EUDRAGIT® NE 30 D dispersion slowly while stirring with overhead stirrer.
3. Talc was homogenized in remaining water for 30 minutes and then added to STEP 2 solution.
4. Resulted suspension was mixed for 15 minutes using overhead stirrer and then passed through 250 micron sieve and used for coating.

Equipment and in Process Coating Parameters for Pellets:
Instrument used: Pam Glatt GPCG 1.1
Silicone tube: 3.0 mm inner diameter
Column height:
Filter shaking mode: Asynchronous
Filter shaking: 5 sec
Filter shaking pause: 250 sec
Air flow mode: Auto
Air flow: 80-90 CFM
Atomisation pressure: 1.0 bar
Inlet temperature: 28° C.-30° C.
Product temperature: 23° C.-24° C.
Spray rate: 3-5 g/min
Curing: 50° C. for 24 hr in Tray Dryer Results Example 14

| API (Metoprolol succinate) Release [%] | | | | | | | | | | |
|---|---|---|---|---|---|---|---|---|---|---|
| Acid stage Release | | Buffer stage Release | | | | | | | | |
| Acid Medium | 2 hr | Buffer Medium | 4 hr | 6 hr | 8 hr | 12 hr | 16 hr | 20 hr | 24 hr | |
| 0.1 N HCl | 14 | pH 6.8 | 18 | 21 | 23 | 26 | 28 | 41 | 72 | Passes |
| 40% EtOH HCl | 14 | pH 6.8 | 22 | 24 | 24 | 26 | 28 | 37 | 61 | |
| 0.1 N HCl | 13 | pH 6.0 | 17 | 19 | 21 | 24 | 26 | 40 | 72 | |
| 0.1 N HCl + $Ca^{++}$ | 15 | pH 6.0 + $Ca^{++}$ | 19 | 21 | 24 | 26 | 31 | 56 | 89 | |
| 0.1 N HCl + $Ca^{++}$ | 16 | pH 6.0 | 21 | 23 | 25 | 28 | 30 | 46 | 78 | |

Outer Layer
Coating of 20% EUDRAGIT® NE 30 D+HPC-LM 4%
Formula for 20% w/w Polymer Coating on 300 g Pellets

| Ingredient | Manufacturer | Solid Content [g] | Quantity/Batch [g] |
|---|---|---|---|
| EUDRAGIT ® NE 30 D | Evonik industries | 60 | 200 |
| Talc (50%) | Luzenac | 30 | 30 |
| HPC-LM (4%) | NIPPON SODA CO., LTD | 2.4 | 2.4 |
| Purified Water | | | 383.6 |
| Total | | 92.4 | 616 |

Solid Content of Coating Suspension: 15% w/w
Procedure for Coating Suspension Preparation:
1. HPC-LM was dissolved in 100 g water using overhead stirrer.

Example 15: (Inventive) Bilayer Coating with Pore Former in Outer Coat

Inner coat: Sodium alginate 20% (by weight calculated to the weight of the core)

Outer Coat:

10% Ethyl Cellulose (by weight calculated to the weight of the core)

PEG 6000 (5% by weight calculated to the weight of Ethyl Cellulose)

Ratio (Solid w/w) Sodium Alginate:Ethyl Cellulose=2:1

Inner Layer

Core: Metoprolol succinate Pellets (18/20# Retained)

Coating of 20% Sodium alginate

Formula for 20% w/w Polymer Coating on 400 g Pellets as Per Example 8

Outer Layer

Coating of 10% Ethyl Cellulose+PEG 6000 (5%)

Formula for 10% w/w Polymer Coating on 400 g Pellets

| Ingredient | Manufacturer | Solid Content [g] | Quantity/Batch [g] |
|---|---|---|---|
| Ethyl Cellulose | N. Shashikant & Co. | 40 | 40 |
| DBS (5% w.r.t. Ethyl Cellulose) | Vertellus | 2 | 2 |
| PEG 6000 (5% w.r.t. Ethyl Cellulose) | SASOL | 2 | 2 |
| IPA (67%) | | — | 339 |
| Acetone (27%) | | — | 136.6 |
| Purified Water (6%) | | — | 30.4 |
| Total | | 44 | 550 |

Solid Content of Coating Suspension: 8% w/w
Procedure for Coating Suspension Preparation:
6. All the ingredients were weighed in required quantity.
7. Dissolve PEG 6000 in water and then add acetone to the dissolved PEG 6000 solution, a clear solution will form.
8. Add DBS to the solution of step 2 and then add IPA to this solution, a clear solution will form.
9. Add Ethyl cellulose to solution of step 3 using overhead stirrer at high speed and stir for 1 hr.
10. Obtained clear coating solution was used for coating.
Note: Please keep solution covered using Aluminium foil during preparation and coating to avoid evaporation of solvents.

Equipment and in Process Coating Parameters for Pellets:
Instrument used: Pam Glatt GPCG 1.1
Silicone tube: 3.0 mm inner diameter
Column height: 15 mm
Nozzle bore: 0.8 mm
Filter shaking mode: Asynchronous
Filter shaking: 4 sec
Filter shaking pause: 50 sec
Air flow mode: Auto
Air flow: 70-90 CFM
Atomisation pressure: 1.1 bar
Inlet temperature: 25° C.-26° C.
Product temperature: 24° C.-25° C.
Spray rate: 3-8 g/min
Curing: 50° C. for 1 hr Fluidization Results Example 15

| | API (Metoprolol succinate) Release [%] | | | | | | | | |
|---|---|---|---|---|---|---|---|---|---|
| Acid stage Release | | Buffer stage Release | | | | | | | |
| Acid Medium | 2 hr | Buffer Medium | 4 hr | 6 hr | 8 hr | 12 hr | 16 hr | 20 hr | 24 hr |
| 0.1 N HCl | 1 | pH 6.8 | 2 | 4 | 9 | 29 | 48 | 61 | 70 | Passes
| 40% EtOH HCl | 2 | pH 6.8 | 4 | 11 | 24 | 45 | 58 | 67 | 74 |
| 0.1 N HCl | 0 | pH 6.0 | 3 | 8 | 15 | 35 | 52 | 64 | 72 |
| 0.1 N HCl + $Ca^{++}$ | 0 | pH 6.0 + $Ca^{++}$ | 3 | 7 | 14 | 34 | 52 | 64 | 73 |
| 0.1 N HCl + $Ca^{++}$ | 0 | pH 6.0 | 3 | 7 | 14 | 35 | 52 | 63 | 71 |

Example 16: (Inventive) Bilayer Coating with Pore Former in Outer Coat

Inner coat: Sodium alginate 20% (by weight calculated to the weight of the core)
Outer Coat:
9% Ethyl Cellulose (by weight calculated to the weight of the core)
Polyvinyl pyrrolidone (PVP K 30) 8%+Dibutylsebacat (DBS) 5% (by weight calculated to the weight of ethyl cellulose)
Ratio (Solid w/w) Sodium Alginate:Ethyl Cellulose=2.22:1
Inner Layer
Core: Metoprolol succinate Pellets (18/20# Retained)
Coating of 20% Sodium alginate
Formula for 20% w/w Polymer Coating on 400 g Pellets as Per Example 8
Outer Layer
Coating of 9% Ethyl Cellulose+PVP K 30 (8%)
Formula for 9% w/w Polymer Coating on 400 g Pellets

| Ingredient | Manufacturer | Solid Content [g] | Quantity/Batch [g] |
|---|---|---|---|
| Ethyl Cellulose | N. Shashikant & Co. | 36 | 36 |
| DBS (5% w.r.t. Ethyl Cellulose) | Vertellus | 1.8 | 1.8 |
| PVP K 30 (8% w.r.t. Ethyl Cellulose) | BASF | 2.88 | 2.88 |
| IPA (70%) | | — | 327.5 |
| Acetone (30%) | | — | 140.3 |
| Total | | 40.68 | 508.48 |

Solid Content of Coating Suspension: 8% w/w
Procedure for Coating Suspension Preparation:
1. All the ingredients were weighed in required quantity.
2. DBS was dissolved in mixture of IPA and Acetone.
3. PVP K 30 was added to solution of Step 2 while stirring with overhead stirrer, continue stirring till clear solution is obtained
4. Add Ethyl cellulose to solution of step 3 using overhead stirrer at high speed and stir for 1 hr.
5. Obtained clear coating solution was used for coating.
Note: Please keep solution covered using Aluminium foil during preparation and coating to avoid evaporation of solvents.

Equipment and in Process Coating Parameters for Pellets:
Instrument used: Pam Glatt GPCG 1.1
Silicone tube: 3.0 mm inner diameter
Column height: 15 mm
Nozzle bore: 0.8 mm
Filter shaking mode: Asynchronous
Filter shaking: 4 sec
Filter shaking pause: 50 sec
Air flow mode: Auto
Air flow: 70-90 CFM
Atomisation pressure: 1.1 bar
Inlet temperature: 25° C.-26° C.
Product temperature: 22° C.-24° C.
Curing: 50° C. for 1 hr Fluidization
Spray rate: 1-8 g/min Results Example 16

| Acid stage Release | | Buffer stage Release | | | | | | | |
|---|---|---|---|---|---|---|---|---|---|
| Acid Medium | 2 hr | Buffer Medium | 4 hr | 6 hr | 8 hr | 12 hr | 16 hr | 20 hr | 24 hr |
| 0.1 N HCl | 0 | pH 6.8 | 2 | 7 | 21 | 53 | 70 | 80 | 86 Passes |
| 40% EtOH HCl | 7 | pH 6.8 | 18 | 27 | 39 | 56 | 68 | 76 | 81 |
| 0.1 N HCl | 0 | pH 6.0 | 1 | 7 | 21 | 53 | 71 | 80 | 85 |
| 0.1 N HCl + $Ca^{++}$ | 0 | pH 6.0 + $Ca^{++}$ | 0 | 0 | 2 | 38 | 58 | 71 | 80 |
| 0.1 N HCl + $Ca^{++}$ | 0 | pH 6.0 | 0 | 0 | 2 | 44 | 64 | 75 | 82 |

API (Metoprolol succinate) Release [%]

The invention claimed is:

1. A pharmaceutical or nutraceutical composition, comprising
   a) core, comprising a pharmaceutical or a nutraceutical active ingredient,
   b) an inner coating layer comprising one or more salts of alginic acid,
   c) an optional water soluble sub coat layer disposed between the core and the inner coating layer, which has essentially no influence on active agent release characteristics,
   d) an outer coating layer comprising
      one or more water-insoluble polymers or copolymers and
      one or more water soluble polymers, selected from the group consisting of water soluble celluloses, polyvinyl pyrrolidones, polyethylene glycols and mixtures thereof, wherein the one or more water-insoluble polymers or copolymers and the one or more water soluble polymers are present within the outer coating layer as a mixture, and
   e) an optional water soluble top coat layer disposed on top of the outer coating layer, which has essentially no influence on the active ingredient release characteristics,
   wherein the ratio by weight of the amount of the one or more salts of alginic acid in the inner coating layer to the amount of the one or more water-insoluble polymer or copolymers in the outer coating layer is from 0.6:1 to less than 2.5:1,
   wherein there are no further coating layers present which would additionally control the release of the active ingredient.

2. The pharmaceutical or nutraceutical composition, according to claim 1, wherein the total amount of the inner coating layer is in the range of 10 to 100% by weight in relation to the total amount of the core by weight.

3. The pharmaceutical or nutraceutical composition, according to claim 1, wherein the one or more salts of alginic acid have a viscosity of 30 to 720 cP in a 1% aqueous solution (weight/weight).

4. The pharmaceutical or nutraceutical composition, according to claim 1, wherein the inner coating layer further comprises up to 70% by weight of one or more pharmaceutically or nutraceutically acceptable excipients relative to the total weight of the inner coating layer.

5. The pharmaceutical or nutraceutical composition, according to claim 1, wherein the release of the pharmaceutical or nutraceutical active ingredient in % under in-vitro conditions in a pH 1.2 medium without ethanol for 2 hours and subsequent change to a buffered pH 6.8 medium does not differ by more than plus/minus 20% (absolute percentage) relative to the release of the pharmaceutical or nutraceutical active ingredient in % under in-vitro conditions in a pH 1.2 medium 40% (v/v) ethanol for 2 hours and subsequent change to a buffered pH 6.8 medium.

6. The pharmaceutical or nutraceutical composition, according to claim 1, wherein the release in % of the pharmaceutical or nutraceutical active ingredient under in-vitro conditions in a pH 1.2 medium without calcium ions for 2 hours and subsequent change to a buffered pH 6.0 medium does not differ by more than plus/minus 20% (absolute percentage) relative to the release in % of the pharmaceutical or nutraceutical active ingredient under in-vitro conditions in a pH 1.2 medium with 1.25 mM calcium ions for 2 hours and subsequent change to a buffered pH 6.0 medium.

7. The pharmaceutical or nutraceutical composition according to claim 1, wherein the release of the pharmaceutical or nutraceutical active ingredient under in-vitro conditions after 2 hours in a pH 1.2 medium according to USP and subsequent change of the medium to a buffered medium of pH 6.8 according to USP is 30 to 100% in a total time from 4 to 16 hours.

8. The pharmaceutical or nutraceutical composition according to claim 1, wherein the one or more water-insoluble polymers or copolymers comprise (meth)acrylate copolymers.

9. The pharmaceutical or nutraceutical composition according to claim 1, wherein the one or more water-insoluble polymers or copolymers comprise a copolymer comprising free-radical polymerized units of more than 95 and up to 100% by weight $C_1$- to $C_4$-alkyl esters of acrylic or of methacrylic acid relative to the total weight of the copolymer and less than 5% by weight of acrylic or methacrylic acid relative to the total weight of the copolymer.

10. The pharmaceutical or nutraceutical composition according to claim 1, wherein the one or more water-insoluble polymers or copolymers are selected from the group consisting of vinyl polymers or copolymers, water-insoluble celluloses, and mixtures thereof.

11. The pharmaceutical or nutraceutical composition according to claim 1, wherein the one or more water-soluble polymers comprise water-soluble celluloses selected from the group consisting of methyl-, ethyl or propyl-ethers of cellulose and mixtures thereof.

12. The pharmaceutical or nutraceutical composition according to claim 1, wherein the outer coating layer further comprises an emulsifier.

13. The pharmaceutical or nutraceutical composition according to claim 1, wherein a release of the pharmaceutical or nutraceutical active ingredient is a sustained release with resistance against the influence of ethanol, resistance against the influence of calcium ions, or both.

14. The pharmaceutical or nutraceutical composition according to claim 6, wherein the release in % of the pharmaceutical or nutraceutical active ingredient under in-vitro conditions in a pH 1.2 medium without calcium ions for 2 hours and subsequent change to a buffered pH 6.0 medium does not differ by more than plus/minus 20% (absolute percentage) relative to the release in % of the pharmaceutical or nutraceutical active ingredient under in-vitro conditions in a pH 1.2 medium with 1.25 mM calcium ions for 2 hours and subsequent change to a buffered pH 6.0 medium with 1.25 mM calcium ions.

15. The pharmaceutical or nutraceutical composition according claim 1, wherein the outer coating layer further comprises up to 20% by weight relative to the total weight of the outer coating layer of a non-ionic emulsifier selected from the group consisting of a polyoxyethylene derivative of a sorbitan ester, a sorbitan ether, and mixtures thereof.

16. The pharmaceutical or nutraceutical composition according to claim 1, wherein either the water soluble sub coat layer or the water soluble top coat layer is present.

17. The pharmaceutical or nutraceutical composition according to claim 1, wherein both the water soluble sub coat layer and the water soluble top coat layer are present.

18. The pharmaceutical or nutraceutical composition according to claim 1, wherein neither the water soluble sub coat layer or the water soluble top coat layer are present.

19. A process for producing the pharmaceutical or nutraceutical composition according to claim 1, the process comprising:
   forming the core comprising the active ingredient by direct compression, compression of dry, wet or sintered granules, extrusion and subsequent rounding off, wet or dry granulation, direct pelleting or by binding powders onto active ingredient-free beads, neutral cores or active ingredient-containing particles and
   applying the inner coating layer and the outer coating layer in the form of aqueous dispersions or organic solutions in spray processes or by fluidized bed spray granulation onto the core.

20. A method for the sustained release of a pharmaceutical or nutraceutical active ingredient, comprising:
   exposing the pharmaceutical or nutraceutical composition according to claim 1 to a medium;
   wherein the release of the pharmaceutical or nutraceutical active ingredient in % under in-vitro conditions in a pH 1.2 medium without ethanol or calcium ions for 2 hours and subsequent change of the medium to a buffered medium of pH 6.8 differs by less than plus/minus 20% (absolute percentage) relative to the release of the pharmaceutical or nutraceutical active ingredient in % under in-vitro conditions in a pH 1.2 medium comprising 40% (v/v) ethanol, 1.25 mM calcium ions, or both for 2 hours and subsequent change of the medium to a buffered pH 6.8 medium.

21. A pharmaceutical or nutraceutical composition, comprising:
   a) a core, comprising a pharmaceutical or a nutraceutical active ingredient,
   b) an inner coating layer comprising one or more salts of alginic acid,
   c) an optional water soluble sub coat layer disposed between the core and the inner coating layer, which has essentially no influence on active agent release characteristics,
   d) an outer coating layer comprising
      one or more water-insoluble polymers or copolymers and one or more water soluble polymers, selected from the group consisting of water soluble celluloses, polyvinyl pyrrolidones, polyethylene glycols and mixtures thereof, wherein the one or more water-insoluble polymers or copolymers and the one or more water soluble polymers are present within the outer coating layer as a mixture, and
   e) an optional water soluble top coat layer disposed on top of the outer coating layer, which has essentially no influence on the active ingredient release characteristics,
   wherein the inner coating layer is in direct contact with the outer coating layer,
   wherein there are no further coating layers present which would additionally control the release of the active ingredient,
   wherein the release of the pharmaceutical or nutraceutical active ingredient in % under in-vitro conditions in a pH 1.2 medium without ethanol or calcium ions for 2 hours and subsequent change of the medium to a buffered medium of pH 6.8 differs by less than plus/minus 20% (absolute percentage) relative to the release of the pharmaceutical or nutraceutical active ingredient in % under in-vitro conditions in a pH 1.2 medium comprising 40% (v/v) ethanol, 1.25 mM calcium ions, or both for 2 hours and subsequent change of the medium to a buffered pH 6.8 medium, and
   wherein the ratio by weight of the amount of the one or more salts of alginic acid in the inner coating layer to the amount of the one or more water-insoluble polymer or copolymers in the outer coating layer is from 0.6:1 to less than 2.5:1.

* * * * *